United States Patent
Wels et al.

(10) Patent No.: US 9,920,132 B2
(45) Date of Patent: *Mar. 20, 2018

(54) CAR-EXPRESSING NK-92 CELLS AS CELL THERAPEUTIC AGENTS

(71) Applicants: CHEMOTHERAPEUTISCHES FORSCHUNGSINSTITUT GEORG-SPEYER-HAUS, Frankfurt am Main (DE); DRK BLUTSPENDEDIENST BADEN-WURTTEMBERG-HESSEN GGMBH, Frankfurt am Main (DE)

(72) Inventors: Winfried Wels, Frankfurt (DE); Kurt Schonfeld, Langen (DE); Torsten Tonn, Dresden (DE); Manuel Grez, Heidelberg (DE); Congcong Zhang, Frankfurt (DE)

(73) Assignees: Chemotherapeutisches Forschungsinstitut Georg-Speyer-Haus, Frankfurt am Main (DE); DRK Blutspendedienst Baden-Wurttemberg-Hessen gGmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,601

(22) Filed: May 19, 2017

(65) Prior Publication Data

US 2017/0283507 A1    Oct. 5, 2017

Related U.S. Application Data

(63) Continuation of application No. 15/319,660, filed as application No. PCT/EP2015/063674 on Jun. 18, 2015.

(30) Foreign Application Priority Data

Jun. 18, 2014   (EP) .................................... 14173020

(51) Int. Cl.
| | | |
|---|---|---|
| *C07K 16/32* | (2006.01) | |
| *C07K 16/28* | (2006.01) | |
| *C07K 14/00* | (2006.01) | |
| *C07K 14/705* | (2006.01) | |
| *C07K 14/725* | (2006.01) | |
| *A61K 39/00* | (2006.01) | |

(52) U.S. Cl.
CPC .......... *C07K 16/32* (2013.01); *C07K 14/7051* (2013.01); *C07K 14/70521* (2013.01); *C07K 16/2863* (2013.01); *A61K 2039/505* (2013.01); *C07K 2317/622* (2013.01); *C07K 2317/73* (2013.01); *C07K 2319/03* (2013.01); *C07K 2319/30* (2013.01)

(58) Field of Classification Search
CPC .... C07K 16/32; C07K 16/28; C07K 14/7051; C07K 14/70521

USPC .................................. 424/185.1, 192.1, 93.2
See application file for complete search history.

(56) References Cited

U.S. PATENT DOCUMENTS

| | | |
|---|---|---|
| 2006/0110360 A1 | 5/2006 | Klingemann |
| 2013/0280285 A1 | 10/2013 | Schonfeld et al. |
| 2016/0046729 A1 | 2/2016 | Schonfeld et al. |
| 2016/0067356 A1 | 3/2016 | Campbell |

FOREIGN PATENT DOCUMENTS

WO    2012031744    3/2012

OTHER PUBLICATIONS

Zhang et al. (Cancer Research, Apr. 2013, vol. 73, Issue 8 Supplement, Abstract: 3967, pp. 1-4).*
Arai et al., Infusion of the allogeneic cell line NK-92 in patients with advanced renal cell cancer or melanoma: a phase I trial, Cytotherapy, 2008;10(6):625-632.
Boissel et al., Transfection with mRNA for CD19 specific chimeric antigen receptor restores NK cell mediated killing of CLL cells, M Leuk Res. 2009;33(9)1255-1259.
Daldrup-Link et al., In vivo tracking of genetically engineered, anti-HER2/neu directed natural killer cells to HER2/neu positive mammary tumors with magnetic resonance imaging, European Radiology, vol. 15. No. 1, Jan. 1, 2005, pp. 4-13.
Duong et al., Engineering T Cell Function Using Chimeric Antigen Receptors Identified Using a DNA Library Approach, Plos One, vol. 8, No. 5, May 7, 2013, p. 8.
Geller et al., Use of allogeneic NK cells for cancer immunotherapy, Immunotherapy 2011; 3:1445-1459.
Gong et al., Characterization of a human cell line (NK-92) with phenotypical and functional characteristics of activated natural killer cells, Leukemia, Apr. 1994, 8(4):652-8.
Grupp et al., Chimeric antigen receptor-modified T cells for acute lymphoid leukemia, N Engl J Med, 2013; 368 (16):1509-1518.
Hynes et al., ERBB receptors and cancer: the complexity of targeted inhibitors, Nat Rev Cancer, 2005; 5(5):341-354.

(Continued)

*Primary Examiner* — Yan Xiao
(74) *Attorney, Agent, or Firm* — Kilpatrick Townsend & Stockton LLP

(57) ABSTRACT

The present invention relates to an ErbB2-specific NK-92 cell or cell line containing a lentiviral vector encoding a chimeric antigen receptor and preferably two vector integration loci in its cellular genome. The present invention further relates to the use of the ErbB2-specific NK-92 cell or cell line in the prevention and/or treatment of cancer, preferably ErbB2-expressing cancers. The present invention further relates to the use of the ErbB2-specific NK-92 cell or cell line as targeted cell therapeutic agent and/or for adoptive cancer immunotherapy. The present invention further relates to a method for generating an ErbB2-specific NK-92 cell or cell line as well as to a method for identifying an ErbB2-specific NK-92 cell or cell line and to the ErbB2-specific NK-92 cell or cell line obtained or identified by the methods as well as their uses.

15 Claims, 8 Drawing Sheets

(56) References Cited

OTHER PUBLICATIONS

International Application No. PCT/EP2015/063674, International Preliminary Report on Patentability dated Dec. 29, 2016, 9 pages.
International Application No. PCT/EP2015/063674, International Search Report and Written Opinion dated Aug. 18, 2015, 14 pages.
EP14173020.0, "Extended European Search Report", Oct. 6, 2014, 9 pages.
Kalos et al., Adoptive T cell transfer for cancer immunotherapy in the era of synthetic biology, Immunity, 2013; 39(1):49-60.
Koch et al., Activating natural cytotoxicity receptors of natural killer cells in cancer and infection, Trends Immunol, 2013; 34(4):182-191.
Maurer-Gebhard et al., Systemic treatment with a recombinant erbB-2 receptor-specific tumor toxin efficiently reduces pulmonary metastases in mice injected with genetically modified carcinoma cells, Cancer Res, 1998; 58 (12)2661-2666.
Müller et al., Expression of a CD20-specific chimeric antigen receptor enhances cytotoxic activity of NK cells and overcomes NK-resistance of lymphoma and leukemia cells, Cancer Immunol Immunother, 2008; 57(3):411-423.
Nowakowska et al., Generation and Qualification of a Gmp Compliant Master Cell Stock of Car Expressing Erbb2-Specific Nk-92 Cells for Clinical Trials, Cytotherapy, vol. 16 (4), Apr. 1, 2014, p. S28.
Sahm et al., Expression of IL-15 in NK cells results in rapid enrichment and selective cytotoxicity of gene-modified effectors that carry a tumor-specific antigen receptor, Cancer Immunol Immunother, 2012; 61(9)1451-1461.
Schambach et al., Woodchuck hepatitis virus post-transcriptional regulatory element deleted from X protein and promoter sequences enhances retroviral vector titer and expression, Gene Ther, 2006; 13(7):641-645.
Schmidt et al., Clonality analysis after retroviral-mediated gene transfer to CD34+ cells from the cord blood of ADA-deficient SCID neonates, Nat Med, 2003; 9(4):463-468.
Tavri et al., Optical imaging of cellular immunotherapy against prostate cancer, Mol Imaging, 2009; 8(1):15-26.
Tonn et al., Treatment of patients with advanced cancer with the natural killer cell line NK-92, Cytotherapy, vol. 15, No. 12, Dec. 2013, pp. 1563-1570.
Uherek et al., Retargeting of natural killer-cell cytolytic activity to ErbB2-expressing cancer cells results in efficient and selective tumor cell destruction, Blood vol. 100, No. 4, Aug. 2002, pp. 1265-1273.

\* cited by examiner

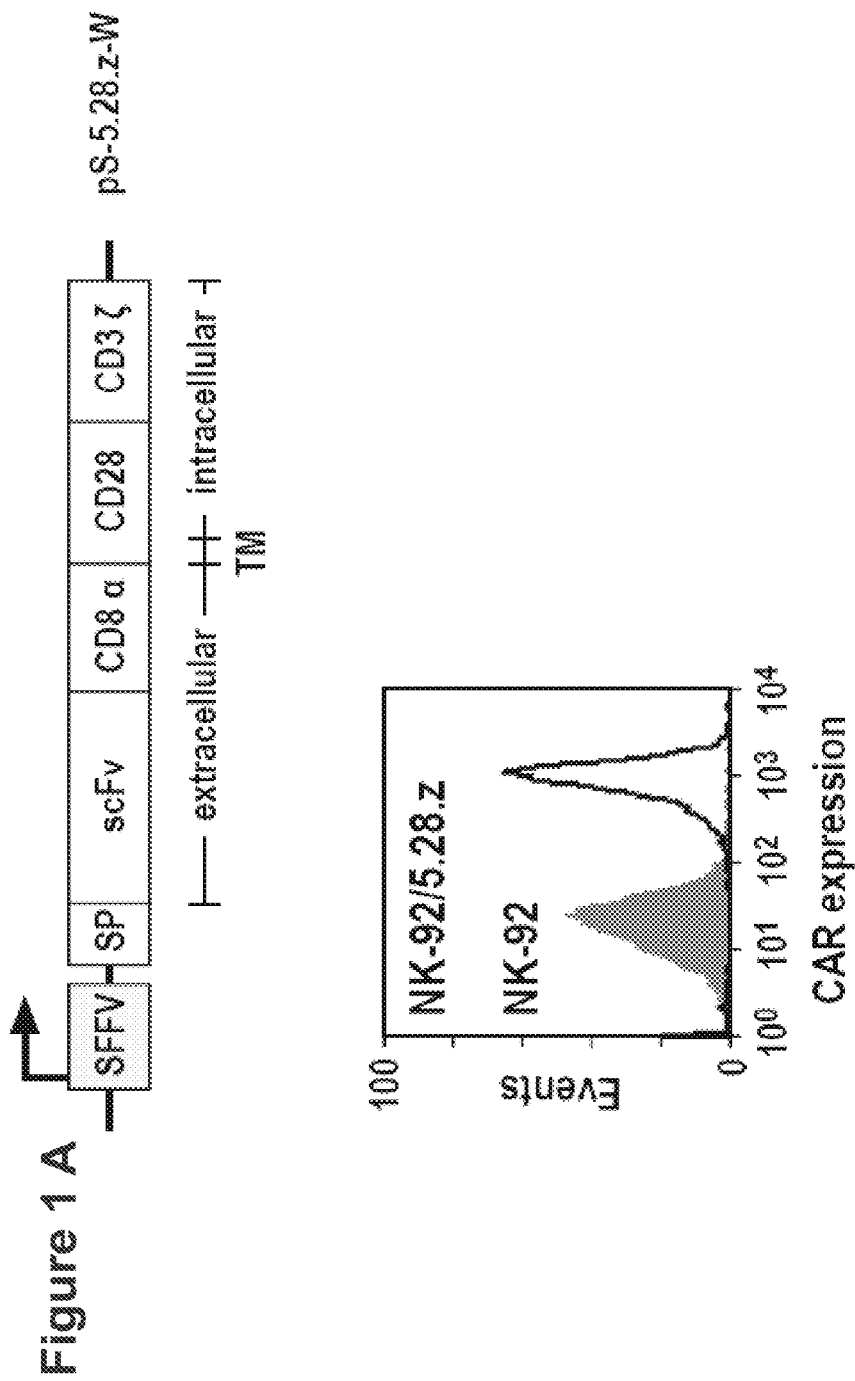

CAR-EXPRESSING NK-92 CELLS AS CELL THERAPEUTIC AGENTS

CROSS-REFERENCE TO RELATED APPLICATIONS

This application is a continuation of U.S. Ser. No. 15/319,660, filed Dec. 16, 2016, which is a 35 USC § 371 national stage entry of International Application No. PCT/EP2015/063674 filed Jun. 18, 2015, which claims the benefit of European Patent Application No. 14173020.0 filed Jun. 18, 2014, each of which are incorporated by reference herein in their entireties.

The present invention relates to an ErbB2-specific NK-92 cell or cell line containing a lentiviral vector encoding a chimeric antigen receptor and preferably two vector integration loci in its cellular genome. The present invention further relates to the use of the ErbB2-specific NK-92 cell or cell line in the prevention and/or treatment of cancer, preferably ErbB2-expressing cancers. The present invention further relates to the use of the ErbB2-specific NK-92 cell or cell line as targeted cell therapeutic agent and/or for adoptive cancer immunotherapy. The present invention further relates to a method for generating an ErbB2-specific NK-92 cell or cell line as well as to a method for identifying an ErbB2-specific NK-92 cell or cell line and to the ErbB2-specific NK-92 cell or cell line obtained or identified by the methods as well as their uses.

BACKGROUND OF THE INVENTION

Natural killer (NK) cells are an important effector cell type for adoptive cancer immunotherapy. Similar to T cells, NK cells can be modified to express chimeric antigen receptors (CARs) to enhance antitumor activity.

Successful application of CAR-modified T cells in patients with CD19-positive malignancies has demonstrated the potency of this approach for adoptive cancer immunotherapy (see e.g. Grupp et al., 2013), and CAR T cells targeting a variety of different tumor antigens are under active clinical development (Kalos et al., 2013). CAR-mediated retargeting of natural killer (NK) cells has been attempted less frequently, and so far no clinical data for such an approach are available. NK cells play an important role in cancer immunosurveillance, and represent an important effector cell type for adoptive cancer immunotherapy (Geller and Miller, 2011). In contrast to T cells, they do not require prior sensitization and recognition of peptide antigens presented in complex with MHC molecules. Instead, their cytotoxicity can be triggered rapidly upon appropriate stimulation through germline-encoded cell surface receptors (Koch et al., 2013), that in part signal through CD3ζ. Hence, CD3ζ-containing CARs readily link to endogenous signaling pathways in NK cells and trigger cytolytic activity (see e.g. Müller et al., 2008). Despite these advances, experience with CAR-engineered NK cells and their clinical development is still limited. Due to efficient antiviral defense mechanisms, gene transfer into NK cells with retro- and lentiviral vectors as well as physical transfection methods are less efficient than in T cells, complicating the generation of large numbers of CAR-expressing cells (Boissel et al., 2009). This restriction can be overcome by employing clinically applicable NK cell lines such as NK-92, which allow isolation and expansion of CAR-expressing cells from a bulk of untransduced cells (Müller et al., 2008).

Phase I studies in cancer patients demonstrated the safety of infusion of unmodified NK-92 cells, which were irradiated prior to application to prevent permanent engraftment. Thereby clinical signs of activity were only observed in a subset of patients (Tonn et al., 2013), likely due to insufficient tumor recognition by the unmodified NK-92 cells which lack a tumor-specific receptor.

The present invention aims to provide improved CAR-engineered NK cells, which are suitable for clinical use, in particular in the treatment of cancers and as targeted cell therapeutic agents.

It is a further objective of the present invention to provide means and methods for generating and molecularly identifying improved CAR-engineered NK cells.

SUMMARY OF THE INVENTION

According to the present invention this object is solved by an ErbB2-specific NK-92 cell or cell line, containing a lentiviral vector encoding a chimeric antigen receptor (CAR) comprising
   an ErbB2-specific scFv antibody fragment, a hinge region, transmembrane and intracellular domains of CD28, and intracellular domain of CD3 zeta,
wherein said vector is genomically integrated (i), preferably in an intergenic region on chromosome 2, and (ii) in the TRAF2 gene on chromosome 9.

According to the present invention this object is solved by providing the NK-92 cell or cell line according to the invention for use in medicine.

According to the present invention this object is solved by providing the NK-92 cell or cell line according to the invention for use in the prevention and/or treatment of cancer, preferably ErbB2-expressing cancers.

According to the present invention this object is solved by providing the NK-92 cell or cell line according to the invention for use as targeted cell therapeutic agent and/or for adoptive cancer immunotherapy.

According to the present invention this object is solved by a method for generating an ErbB2-specific NK-92 cell or cell line, comprising the steps of:
(1) providing a vector for transducing NK-92 cells,
(2) transducing NK-92 cells with said vector,
(3) deriving/generating single cell clones by limiting dilution;
(4) identifying CAR-expressing cells by flow cytometric analysis with ErbB2-Fc fusion protein,
(5) selecting cell clone(s) which display high and stable CAR-expression during continuous culture,
(6) evaluating cytotoxic activity of the retargeted cells against ErbB2-expressing cells,
(7) evaluating cytotoxic activity of the retargeted cells against ErbB2-negative cells,
(8) selecting cell clone(s) which display high cytotoxicity against ErbB2-expressing cells and low or no cytotoxicity against ErbB2-negative cells, and
(9) determining number and position of vector integration, and selecting the cell clones exhibiting vector intergration in an intergenic region on chromosome 2 and in the TRAF2 gene on chromosome 9.

According to the present invention this object is solved by a method for identifying an ErbB2-specific NK-92 cell or cell line, comprising the steps of:
   determining number and position of vector integration in cell (clones), and selecting the cell (clones) exhibiting vector integration in an intergenic region on chromosome 2 and in the TRAF2 gene on chromosome 9.

According to the present invention this object is solved by an NK-92 cell or cell line obtained or identified by the methods according to the invention.

According to the present invention this object is solved by providing the NK-92 cell or cell line obtained or identified by the methods according to the invention for use in the prevention and/or treatment of cancer, preferably ErbB2-expressing cancers.

According to the present invention this object is solved by providing the NK-92 cell or cell line obtained or identified by the methods according to the invention for use as targeted cell therapeutic agent and/or for adoptive cancer immunotherapy.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Clinically Usable CAR-Expressing Human NK-92 Cells

As described above, the present invention provides an ErbB2-specific NK-92 cell or cell line, The ErbB2-specific NK-92 cell or cell line of the present invention contains
 a lentiviral vector encoding a chimeric antigen receptor comprising
  an ErbB2-specific scFv antibody fragment, a hinge region, transmembrane and intracellular domains of CD28, and intracellular domain of CD3 zeta.

The ErbB2-specific NK-92 cell or cell line preferably contains two vector integration loci in its cellular genome.

The ErbB2-specific NK-92 cell or cell line is characterized in that said vector is genomically integrated (i), preferably in an intergenic region on chromosome 2, and (ii) in the TRAF2 gene on chromosome 9.

The unmodified NK-92 cell or cell line is known in the art. See e.g. Gong et al., 1994 or WO 98/49268 A1. NK-92 cells are deposited with the American Type Tissue Collection (ATCC no. CRL-2407).

Vector Integration

The ErbB2-specific NK-92 cell or cell line can be molecularly characterized and identified by said two vector integrations.

Preferably, the NK-92 cell or cell line of the present invention is characterized in that by PCR analysis of the genomic DNA of said cell or cell line at least one of the following amplification products is/are obtained:
 PCR with primers of SEQ ID NOs. 1 and 2 yields an amplification product with the nucleotide sequence of SEQ ID NO. 9;
 PCR with primers of SEQ ID NOs. 3 and 4 yields an amplification product with the nucleotide sequence of SEQ ID NO. 10;
 PCR with primers of SEQ ID NOs. 5 and 6 yields an amplification product with the nucleotide sequence of SEQ ID NO. 11;
 PCR with primers of SEQ ID NOs. 7 and 8 yields an amplification product with the nucleotide sequence of SEQ ID NO. 12.

PCR analysis of genomic DNA of the cell or cell line of the invention with oligonucleotide primers hybridizing to genomic and vector DNA sequences adjacent to 5' and 3' junction sites of chromosomal and integrated vector sequences (namely the oligonucleotide primers specified in SEQ ID NO. 1 and 2, 3 and 4, 5 and 6, 7 and 8) yield amplification products of defined length and sequence (namely the PCR fragments specified in SEQ ID NO. 9, 10, 11, 12), confirming the vector integrations and molecularly identifying the cell (clone) NK-92 of the present invention.

1) Oligonucleotide primers hybridizing to genomic and vector DNA sequences adjacent to 5' and 3' junction sites of chromosomal and integrated vector sequences:

a) CAR vector integration in TRAF2 gene
a-1) 5' part of vector integration
Forward PCR primer TRAF2-F1:

CTTCAGCAGGGACCAGAAACAA [SEQ ID NO. 1]

Reverse PCR primer CAR-R1 (vector sequence underlined)

<u>CCGCTTAATACTGACGCTCTCG</u> [SEQ ID NO. 2]

a-2) 3' part of vector integration
Forward PCR primer CAR-F1 (vector sequence underlined)

<u>ATCGCCACGGCAGAACTCA</u> [SEQ ID NO. 3]

Reverse PCR primer TRAF2-R1

GACCCTTCACCCAACGCTTAG [SEQ ID NO. 4]

b) CAR vector integration in intergenic region of chromosome 2
b-1) 5' part of vector integration
Forward PCR primer IGCHR2-F1

TCAGTGGAATGGGCAGCTTCAAGT [SEQ ID NO. 5]

Reverse PCR primer CAR-R2 (vector sequence underlined)

<u>TTCAGCAAGCCGAGTCCTGCGT</u> [SEQ ID NO. 6]

b-2) 3' part of vector integration
Forward PCR primer CAR-F2 (vector sequence underlined)

<u>ACTGATAATTCCGTGGTGTTGT</u> [SEQ ID NO. 7]

Reverse PCR primer IGCHR2_CAR-R1 (vector sequence underlined)

CACTGTGGCTCAC<u>TGCTAGA</u> [SEQ ID NO. 8]

2) Amplification products of defined length and sequence:
a) Amplification product of CAR vector integration in TRAF2 gene
CAR vector integration in TRAF2 gene
5' part of vector integration
PCR product TRAF2-CAR (5') from genomic DNA of NK-92/5-28.z cells
Primers: TRAF2-F1 (SEQ ID NO. 1), CAR-R1 (SEQ ID NO. 2)
lower case letters: TRAF2 gene
upper case letters: vector sequence
Length: 587 nucleotides

```
                                                        SEQ ID NO. 9
         cttcagcagggaccagaaacaaaactcacactctttcttctctgagttga       50 gactggaaaaatgaaagattgttttaggggaaacttgagggaacagtctg      100 ggcagcctgcagggcatggccctgttcctccagggctgggaaagtcagca      150 ctgctttctggtggcgaACTGGAAGGGCTAATTCACTCCCAACGAAGACA      200

AGATCTGCTTTTTGCTTGTACTGGGTCTCTCTGGTTAGACCAGATCTGAG      250

CCTGGGAGCTCTCTGGCTAACTAGGGAACCCACTGCTTAAGCCTCAATAA      300

AGCTTGCCTTGAGTGCTTCAAGTAGTGTGTGCCCGTCTGTTGTGTGACTC      350

TGGTAACTAGAGATCCCTCAGACCCTTTTAGTCAGTGTGGAAAATCTCTA      400

GCAGTGGCGCCCGAACAGGGACTTGAAAGCGAAAGGGAAACCAGAGGAGC      450

TCTCTCGACGCAGGACTCGGCTTGCTGAAGCGCGCACGGCAAGAGGCGAG      500

GGGCGGCGACTGGTGAGTACGCCAAAAATTTTGACTAGCGGAGGCTAGAA      550

GGAGAGAGATGGGTGCGAGAGCGTCAGTATTAAGCGG                   587
``` b) Amplification product of CAR vector integration in TRAF2 gene
CAR vector integration in TRAF2 gene
3' part of vector integration
PCR product CAR-TRAF2 (3') from genomic DNA of NK-92/5-28.z cells
Primers: CAR-F1 (SEQ ID NO. 3), TRAF2-R1 (SEQ ID NO. 4)
lower case letters: TRAF2 gene
upper case letters: vector sequence
Length: 503 nucleotides

```
                                                        SEQ ID NO. 10
         ATCGCCACGGCAGAACTCATCGCCGCCTGCCTTGCCCGCTGCTGGACAGG       50

GGCTAGGTTGCTGGGCACTGATAATTCCGTGGTGTTGTCGAATTCGATAC      100

TCGAGGTCGAGGCAATTCGAGCTCGGTACCTTTAAGACCAATGACTTACA      150

AGGCAGCTGTAGATCTTAGCCACTTTTTAAAAGAAAAGGGGGGACTGGAA      200

GGGCTAATTCACTCCCAACGAAGACAAGATCTGCTTTTTGCTTGTACTGG      250

GTCTCTCTGGTTAGACCAGATCTGAGCCTGGGAGCTCTCTGGCTAACTAG      300

GGAACCCACTGCTTAAGCCTCAATAAAGCTTGCCTTGAGTGCTTCAAGTA      350

GTGTGTGCCCGTCTGTTGTGTGACTCTGGTAACTAGAGATCCCTCAGACC      400

CTTTTAGTCAGTGTGGAAAATCTCTAGCAccttccctctgcagctgctgg      450 ctcagccgattgtatatgctgggagctctgcactaagcgttgggtgaagg      500 gtc                                                     503
``` c) Amplification product of CAR vector integration in intergenic region of chromosome 2
CAR vector integration in intergenic region of chromosome 2
5' part of vector integration
PCR product IGCHR2-CAR (5') from genomic DNA of NK-92/5-28.z cells
Primers: IGCHR2-F1 (SEQ ID NO. 5), CAR-R2 (SEQ ID NO. 6)
lower case letters: intergenic region chromosome 2
upper case letters: vector sequence
Length: 679 nucleotides

```
                                                        SEQ ID NO. 11
         tcagtggaatgggcagcttcaagttgatgtcatttcaatagtaacttatt       50 tcagtctacatacttcccaagaatgcaccatctcttttttatgtatttat      100 tattttgagaaagagtctcactctgtcgcccaggctggagtgcaatggca      150
```

```
                                                            -continued
tgatcttggctcactgtaacctccgtctcctgggttcaagccattctcct          200 gtctcagcctcccgggtagtggggttataggcacacaccaccacgcccgg          250 ctaattttgtattttagtaaagatggggtttcaccatgttggccaggc            300 tgggctcaaactcttgacttcaggtgatccgcccaccttggcctcccaaa          350 gtgctgggatgacaggcACTGGAAGGGCTAATTCACTCCCAACGAAGACA          400

AGATCTGCTTTTTGCTTGTACTGGGTCTCTCTGGTTAGACCAGATCTGAG          450

CCTGGGAGCTCTCTGGCTAACTAGGGAACCCACTGCTTAAGCCTCAATAA          500

AGCTTGCCTTGAGTGCTTCAAGTAGTGTGTGCCCGTCTGTTGTGTGACTC          550

TGGTAACTAGAGATCCCTCAGACCCTTTTAGTCAGTGTGGAAAATCTCTA          600

GCAGTGGCGCCCGAACAGGACTTGAAAGCGAAAGGGAAACCAGAGGAGC           650

TCTCTCGACGCAGGACTCGGCTTGCTGAA                               679
``` d) Amplification product of CAR vector integration in intergenic region of chromosome 2
CAR vector integration in intergenic region of chromosome 2
3' part of vector integration
PCR product CAR-IGCHR2 (3') from genomic DNA of NK-92/5-28.z cells
Primers: CAR-F2 (SEQ ID NO. 7), IGCHR2_CAR-R1 (SEQ ID NO. 8)
lower case letters: intergenic region chromosome 2
upper case letters: vector sequence
Length: 376 nucleotides

```
                                                      SEQ ID NO. 12
ACTGATAATTCCGTGGTGTTGTCGAATTCGATACTCGAGGTCGAGGCAAT           50

TCGAGCTCGGTACCTTTAAGACCAATGACTTACAAGGCAGCTGTAGATCT          100

TAGCCACTTTTTAAAAGAAAAGGGGGGACTGGAAGGGCTAATTCACTCCC          150

AACGAAGACAAGATCTGCTTTTTGCTTGTACTGGGTCTCTCTGGTTAGAC          200

CAGATCTGAGCCTGGGAGCTCTCTGGCTAACTAGGGAACCCACTGCTTAA          250

GCCTCAATAAAGCTTGCCTTGAGTGCTTCAAGTAGTGTGTGCCCGTCTGT          300

TGTGTGACTCTGGTAACTAGAGATCCCTCAGACCCTTTTAGTCAGTGTGG          350

AAAATCTCTAGCAgtgagccacagtg                                  376
```

Reduced Natural Cytotoxicity and High Specific Cytotoxicity

Preferably, the NK-92 cell or cell line of the present invention is characterized in that:
the NK-92 cell or cell line shows reduced or no natural cytotoxicity, i.e. reduced or no cytotoxicity to ErbB2-negative cells which are lysed by unmodified NK-92 cells,
and/or
the NK-92 cell or cell line shows increased specific cytotoxicity, i.e. increased cytotoxicity to ErbB2-expressing tumor cells compared to unmodified NK-92 cells.

Said reduced natural cytotoxicity constitutes an important safety feature of the cell or cell line of the invention, in particular in view of a clinical use.

The NK-92 cell or cell line of the present invention—in contrast to unmodified NK-92 cells—lyse ErbB2-expressing tumor cells with high efficiency, but are less likely than unmodified NK-92 cells to attack ErbB2-negative non-target cells.

Further Features

In one embodiment, the ErbB2-specific scFv antibody fragment comprises or consists of the amino acid sequence of SEQ ID NO. 13 (scFv FRP5) and/or is encoded by the nucleotide sequence of SEQ ID NO. 14.

ErbB2-specific scFv FRP5 is further described in EP 2 164 516 B1 and U.S. Pat. No. 7,887,801 B2.

Chimeric antigen receptors (CARs) are known in the art. The ErbB2-specific CAR used in the present invention comprises:
(i) an ErbB2-specific scFv antibody fragment,
(ii) a hinge region,
(iii) transmembrane and intracellular domains of CD28, and intracellular domain of CD3 zeta.

In one embodiment, the chimeric antigen receptor (CAR) comprises or consists of the amino acid sequence of SEQ ID NO. 15 and/or is encoded by the nucleotide sequence of SEQ ID NO. 16.

Suitable CARs are further described in WO 2012/031744.

For example, the lentiviral transfer plasmid pS-5.28.z-W encoding under the transcriptional control of the Spleen Focus Forming Virus promoter (SFFV) the chimeric antigen receptor (CAR) consisting of an immunoglobulin heavy chain signal peptide, the ErbB2-specific scFv (FRP5) antibody fragment, a hinge region (CD8α), followed by transmembrane and intracellular domains of CD28 and the intracellular domain of CD3ζ. The CAR-encoding sequence is flanked by 5' and 3' long terminal repeats (LTR) of the vector.

Natural killer (NK) cells are an important effector cell type for adoptive cancer immunotherapy. Similar to T cells, NK cells can be modified to express chimeric antigen receptors (CARs) to enhance antitumor activity, but experience with CAR-engineered NK cells is limited and data on clinical development are lacking. Here, the inventors redirected clinically usable human NK-92 cells to the tumor-associated ErbB2 (HER2) antigen expressed at elevated levels by many cancers of epithelial origin.

Following GMP-compliant procedures, the inventors generated an NK-92/5.28.z single cell clone expressing an ErbB2-specific CAR with CD28 and CD3ζ signaling domains.

Vector integrations in the NK-92/5.28.z cell clone were mapped by linear amplification-mediated PCR and DNA sequencing following established procedures (Schmidt et al., 2003), which revealed one vector integration each in an intergenic region on chromosome 2, and in the TRAF2 gene on chromosome 9. As discussed above, PCR analysis of genomic DNA with oligonucleotide primers hybridizing to genomic and vector DNA sequences adjacent to 5' and 3' junction sites of chromosomal and integrated vector sequences (e.g. the oligonucleotide primers specified in SEQ ID NO. 1 and 2, 3 and 4, 5 and 6, 7 and 8) yield amplification products of defined length and sequence (e.g. the PCR fragments specified in SEQ ID NO. 9, 10, 11, 12), confirming the vector integrations and molecularly identifying the cell clone NK-92/5.28.z.

NK-92/5.28.z cells efficiently lysed ErbB2-expressing and otherwise NK-resistant tumor cells in vitro, but did not lyse ErbB2-negative cells resistant to unmodified NK-92. Unexpectedly, NK-92/5.28.z cells also displayed reduced cytotoxicity to ErbB2-negative cells which are readily lysed by unmodified NK-92 cells. This constitutes an important safety feature of NK-92/5.28.z cells which in contrast to unmodified NK-92 cells lyse ErbB2-expressing tumor cells with high efficiency, but are less likely than unmodified NK-92 cells to attack ErbB2-negative non-target cells. Specific recognition of tumor cells and antitumor activity were retained in vivo, resulting in homing of NK-92/5.28.z cells to orthotopic breast carcinoma xenografts and reduction of pulmonary metastasis of renal cell carcinoma cells. γ-irradiation as a potential safety measure for clinical application prevented replication of the cells, while in vitro and in vivo antitumoral activity were preserved.

A particularly preferred ErbB2-specific NK-92 cell or cell line of the invention is the NK-92 cell or cell line identified as NK-92/5.28.z which was deposited on Jun. 11, 2014 at the Leibniz Institute DSMZ—German Collection of Microorganisms and Cell Cultures GmbH, Inhoffenstr. 7B, 38124 Braunschweig, Germany, under accession number DSM ACC3244.

The present invention demonstrates that it is feasible to engineer CAR-expressing NK cells as a clonal, molecularly and functionally well-defined and continuously expandable cell therapeutic agent, and suggest NK-92/5.28.z cells as a promising candidate for clinical development.

Medical Uses

As described above, the present invention provides the ErbB2-specific NK-92 cell or cell line according to the invention for use in medicine.

As described above, the present invention provides the NK-92 cell or cell line according to the invention for use in the prevention and/or treatment of cancer, preferably ErbB2-expressing cancers.

Preferably, the cancer, preferably the ErbB2-expressing cancers, is/are selected from
breast cancer,
ovarian cancer,
gastric cancer,
prostate cancer,
squamous cell carcinoma,
head and neck cancer,
colon cancer,
pancreatic cancer,
uterine cancer,
renal cell cancer,
glioblastoma,
medulloblastoma,
sarcoma
lung cancer.

In a preferred embodiment, the cells are pre-treated by irradiation, preferably by γ-irradiation.

Said irradiation may be included as a safety measure.

As described above, the present invention provides the NK-92 cell or cell line according to the invention for use as targeted cell therapeutic agent and/or for adoptive cancer immunotherapy.

A "cell therapeutic agent", in particular a "targeted cell therapeutic agent" or "targeted allogeneic cell therapeutic agent" refers to an immune cell suitable for application for adoptive cancer immunotherapy, which is genetically modified to express an antigen receptor that specifically recognizes a defined antigen expressed on the surface of a target tumor cell.

"Adoptive, target-cell specific immunotherapy" or "adoptive cancer immunotherapy" or "adoptive cell therapy (ACT)" refers to a form of therapy in which immune cells are transferred to tumor-bearing hosts. The immune cells have antitumor reactivity and can mediate direct or indirect antitumor effects.

Genetic engineering of NK-92 cells with CARs, such as provided by this invention, is very suitable for ACT and the treatment of cancer.

Preferably, the use comprises a pre-treatment of the cells by irradiation, preferably γ-irradiation.

Said irradiation may be included as a safety measure.

Method for Generating an ErbB2-Specific NK-92 Cell or Cell Line

As described above, the present invention provides a method for generating an ErbB2-specific NK-92 cell or cell line.

Said methods further allows to molecularly identify the ErbB2-specific NK-92 cell or cell line generated.

Said method comprises the steps of:
(1) providing a vector for transducing NK-92 cells,
(2) transducing NK-92 cells with said vector,
(3) deriving/generating single cell clones by limiting dilution;
(4) identifying CAR-expressing cells by flow cytometric analysis with ErbB2-Fc fusion protein,
(5) selecting cell clone(s) which display high and stable CAR-expression during continuous culture,
(6) evaluating cytotoxic activity of the retargeted cells against ErbB2-expressing cells,
(7) evaluating cytotoxic activity of the retargeted cells against ErbB2-negative cells,
(8) selecting cell clone(s) which display high cytotoxicity against ErbB2-expressing cells and low or no cytotoxicity against ErbB2-negative cells, and
(9) determining number and position of vector integration, and selecting the cell clones exhibiting vector intergration in an intergenic region on chromosome 2 and in the TRAF2 gene on chromosome 9.

The vector for transducing NK-92 cells of step (1) is an integrating vector, preferably a lentiviral vector.

An example for a suitable lentiviral vector is lentiviral transfer plasmid pHR'SIN-cPPT-WPREmut vector (Schambach et al., 2006).

Further suitable lentiviral vectors are known to the skilled person.

The lentiviral vector encodes a chimeric antigen receptor (CAR) comprising
an ErbB2-specific scFv antibody fragment,
a hinge region,
transmembrane and intracellular domains of CD28,
and intracellular domain of CD3 zeta.

The lentiviral vector can be generated following established methodology known to a skilled person.

A suitable example for an ErbB2-specific scFv antibody fragment is scFv FRP5.

For example, the ErbB2-specific scFv antibody fragment comprises or consists of the amino acid sequence of SEQ ID NO. 13 (scFv FRP5) and/or is encoded by the nucleotide sequence of SEQ ID NO. 14.

ErbB2-specific scFv FRP5 is further described in EP 2 164 516 B1 and U.S. Pat. No. 7,887,801 B2.

Chimeric antigen receptors (CARs) are known in the art. The ErbB2-specific CAR used in the present invention comprises:
(i) an ErbB2-specific scFv antibody fragment,
(ii) a hinge region,
(iii) transmembrane and intracellular domains of CD28, and intracellular domain of CD3 zeta.

In one embodiment, the chimeric antigen receptor (CAR) comprises or consists of the amino acid sequence of SEQ ID NO. 15 and/or is encoded by the nucleotide sequence of SEQ ID NO. 16.

Suitable examples for chimeric antigen receptors (CARs) comprising an ErbB2-specific scFv antibody fragment are further known, such as described in WO 2012/031744.

Said ErbB2-negative cells are used for evaluating or testing the natural cytotoxicity/endogenous, CAR-independent cytotoxicity of the cell clones.

The cytotoxicity assays in step (6) and/or (7) are preferably also carried out with unmodified NK-92 cells (ATCC no. CRL-2407) and the results are compared with the results of the tested cell clones.

In step (8), the cell clone(s) are selected which display high cytotoxicity against ErbB2-expressing cells and low or no cytotoxicity against ErbB2-negative cells.

Step (9) preferably comprises determining number and position of vector integration by linear amplification-mediated PCR (LAM-PCR) and DNA sequencing, and confirmation by PCR analysis of genomic DNA.

Suitable primers for the PCR analysis of genomic DNA and their respective amplification products are, for example (in an embodiment with a lentiviral vector):

Vector integration site: CAR vector integration in TRAF2 gene:

|  | Forward Primer | Reverse Primer | Amplification Product |
|---|---|---|---|
| 5' part | TRAF2-F1: CTTCAGCAGGGACCAGAAACAA [SEQ ID NO. 1] | CAR-R1: CCGCTTAATACTGACGCTCTCG [SEQ ID NO. 2] | TRAF2-CAR (5') 587 bp [SEQ ID NO. 9] |
| 3' part | CAR-F1: ATCGCCACGGCAGAACTCA [SEQ ID NO. 3] | TRAF2-R1: GACCCTTCACCCAACGCTTAG [SEQ ID NO. 4] | CAR-TRAF2 (3') 503 bp [SEQ ID NO. 10] |

Vector integration site: CAR vector integration in intergenic region of chromosome 2:

|  | Forward Primer | Reverse Primer | Amplification Product |
|---|---|---|---|
| 5' part | IGCHR2-F1: TCAGTGGAATGGGCAGCTTCAAGT [SEQ ID NO. 5] | CAR-R2: TTCAGCAAGCCGAGTCCTGCGT [SEQ ID NO. 6] | IGCHR2-CAR (5') 679 bp [SEQ ID NO. 11] |
| 3' part | CAR-F2: ACTGATAATTCCGTGGTGTTGT [SEQ ID NO. 7] | IGCHR2_CAR-R1: CACTGTGGCTCACTGCTAGA [SEQ ID NO. 8] | IGCHR2-CAR (3') 376 [SEQ ID NO. 12] |

Step (1) preferably comprises producing VSV-G pseudotyped lentiviral vector particles.

Step (2) is preferably carried out by following GMP-compliant procedures.

The NK-92 cells of step (2) are preferably human NK-92 cells.

Step (5) preferably comprises selecting cell clone(s) which display high and stable CAR-expression during continuous culture.

Steps (6) and (7) comprise in vitro cytotoxicity assays, such as FACS based assays, preferably carried out at different effector to target ratios (E/T).

Suitable ErbB2-expressing cells are ErbB2-expressing tumor cells, such as murine renal cell carcinoma cells stably expressing human ErbB2 (Renca-lacZ/ErbB2) or MDA-MB453 human breast carcinoma cells (ATCC no. HTB-131).

Said ErbB2-negative cells are used for evaluating or testing the specific cytotoxicity of the cell clones.

Suitable ErbB2-negative cells are NK-sensitive but ErbB2-negative cells, such as human K562 erythroleukemia cells (ATCC no. CCL-243).

As described above, the present invention provides an NK-92 cell or cell line obtained by the method according to the invention.

Method for Identifying an ErbB2-Specific NK-92 Cell or Cell Line

As described above, the present invention provides a method for identifying an ErbB2-specific NK-92 cell or cell line.

Said method comprises the steps of:
determining number and position of vector integration in cell (clones), and selecting the cell (clones) exhibiting vector integration in an intergenic region on chromosome 2 and in the TRAF2 gene on chromosome 9.

As discussed above, the method preferably comprises determining number and position of vector integration by linear amplification-mediated PCR (LAM-PCR) and DNA sequencing, and confirmation by PCR analysis of genomic DNA.

Suitable primers for the PCR analysis of genomic DNA and their respective amplification products are, for example (in an embodiment with a lentiviral vector), as described above.

As described herein above, preferably, the cell (clone) is characterized in that by PCR analysis of the genomic DNA of said cell (clone) at least one of the following amplification products is obtained:

PCR with primers of SEQ ID NOs. 1 and 2 yields an amplification product with the nucleotide sequence of SEQ ID NO. 9;

PCR with primers of SEQ ID NOs. 3 and 4 yields an amplification product with the nucleotide sequence of SEQ ID NO. 10;

PCR with primers of SEQ ID NOs. 5 and 6 yields an amplification product with the nucleotide sequence of SEQ ID NO. 11;

PCR with primers of SEQ ID NOs. 7 and 8 yields an amplification product with the nucleotide sequence of SEQ ID NO. 12.

As described above, the present invention provides an NK-92 cell or cell line identified by the method according to the invention.

As described above, the present invention provides the NK-92 cell or cell line obtained or identified by the methods according to the invention for use in the prevention and/or treatment of cancer, preferably ErbB2-expressing cancers.

Preferably, the cancer, preferably the ErbB2-expressing cancers, is/are selected from:
breast cancer,
ovarian cancer,
gastric cancer,
prostate cancer,
squamous cell carcinoma,
head and neck cancer,
colon cancer,
pancreatic cancer,
uterine cancer,
renal cell cancer,
glioblastoma,
medulloblastoma,
sarcoma, and
lung cancer.

In a preferred embodiment, the cells are pre-treated by irradiation, preferably by γ-irradiation.

Said irradiation may be included as a safety measure.

As described above, the present invention provides the NK-92 cell or cell line obtained or identified by the methods according to the invention for use as targeted (allogeneic) cell therapeutic agent and/or for adoptive cancer immunotherapy.

Preferably, the use comprises a pre-treatment of the cells by irradiation, preferably γ-irradiation.

Said irradiation may be included as a safety measure.

Methods of Prevention and/or Treatment

According to the present invention this object is solved by a method for the prevention and/or treatment of cancer (herein after "treatment method").

The cancer is preferably the ErbB2-expressing cancers, which is/are preferably selected from:
breast cancer,
ovarian cancer,
gastric cancer,
prostate cancer,
squamous cell carcinoma,
head and neck cancer,
colon cancer,
pancreatic cancer,
uterine cancer,
renal cell cancer,
glioblastoma,
medulloblastoma,
sarcoma, and
lung cancer.

Preferably, said treatment method comprises or includes adoptive cancer immunotherapy.

Said treatment method comprises
administering to a subject in a therapeutically effective amount
(a) NK-92 cells according to the present invention or NK-92 cells obtained by the method according to the present invention, and
(b) optionally, respective excipient(s).

A "therapeutically effective amount" of the NK-92 cells of this invention refers to the amount that is sufficient to treat the respective disease (cancer) or achieve the respective outcome of the adoptive, target-cell specific immunotherapy.

PREFERRED EMBODIMENT

According to the present invention, CAR-engineered NK-92 cells were developed as a targeted allogeneic cell therapeutic agent. Here, we describe the generation and the molecular and functional characterization of a clonal ErbB2-specific NK-92 cell line suitable for clinical applications. These NK-92/5.28.z cells were derived from a single cell clone after lentiviral transduction with a vector encoding a second generation CAR that targets the ErbB2 (HER2) receptor tyrosine kinase, a tumor-associated self-antigen expressed at elevated levels by many human cancers of epithelial origin (Hynes and Lane, 2005).

Following GMP-compliant procedures, we generated an NK-92/5.28.z single cell clone expressing an ErbB2-specific CAR with CD28 and CD3ζ signaling domains. Vector integrations were mapped by linear amplification-mediated PCR and DNA sequencing. In vivo tumor homing and antimetastatic activity were evaluated in NOD-SCID IL2Rγ$^{null}$ (NSG) mouse models.

ErbB2-specific NK-92/5.28.z cells efficiently lysed ErbB2-expressing tumor cells in vitro that were resistant to unmodified NK-92 cells. Importantly, specific recognition of ErbB2-positive tumor cells and antitumoral activity were retained in vivo, resulting in homing of NK-92/5.28.z cells to orthotopic breast carcinoma xenografts and reduction of pulmonary metastasis of renal cell carcinoma cells in murine models.

The data shown in the present application demonstrate successful targeting of human NK-92 cells to the tumor-associated cell surface antigen ErbB2 by expression of a humanized and codon-optimized second-generation CAR. Following GMP-compliant procedures, we established from a molecularly defined single cell clone a continuously expanding CAR-modified cell line suitable for clinical development. These NK-92/5.28.z cells display stable CAR expression upon prolonged culture and target-antigen-specific cytotoxicity in vitro and in vivo. The possibility to fully characterize this cell clone at the molecular and cellular levels adds an important degree of safety for the clinical application of the clone, in contrast to the heterogeneous composition of CAR-modified primary NK and T cells, in which no exhaustive molecular analysis is possible.

In mice fluorochrome-labeled NK-92/5.28.z cells selectively enriched in ErbB2-positive orthotopic breast carcinoma xenografts within 24 hours after intravenous injection, while unmodified NK-92 cells failed to accumulate in tumors. This demonstrates that NK-92/5.28.z cells retain target cell specificity in vivo, and are capable of penetrating tissues and homing to distant tumor sites. In an experimental metastasis model based on ErbB2-expressing renal cell carcinoma cells, intravenous injection of NK-92/5.28.z cells reduced metastasis formation in different experiments by 50% or more, while unmodified NK-92 cells failed to affect outgrowth of pulmonary tumor nodules. Importantly, in vivo antitumor activity of NK-92/5.28.z cells irradiated with 10 Gy was the same as that of non-irradiated cells. This may be relevant for future clinical application of NK-92/5.28.z, where irradiation of cells may be included as a safety measure as previously done in phase I clinical trials with unmodified NK-92 cells (Arai et al. 2008; Tonn et al., 2013).

Immune cells in tumor patients are often functionally compromised due to the immunosuppressive activity of the cancer. Hence, for adoptive cancer immunotherapy with NK cells, donor-derived allogeneic cells are being preferred since they do not recognize tumor cells as 'self', thereby bypassing inhibitory signals (Geller and Miller, 2011). We have shown, that this advantage can be extended to CAR-engineered NK-92 cells.

Our data demonstrate that it is feasible to develop CAR-engineered NK-92 cells in a similar manner as a clonal, molecularly and functionally well-defined and continuously expandable off-the-shelf cell therapeutic agent with selective and markedly enhanced antitumor activity in vitro and in vivo. Such cells are clinically useful for the treatment of various ErbB2-positive malignancies. Thereby the potent antitumor activity, the immediate availability as a fully characterizable cell product, and the lack of obvious risks of manufacturing failures makes these cells a valid and cost-effective alternative to CAR-modified patient T cells.

The following examples and drawings illustrate the present invention without, however, limiting the same thereto.

BRIEF DESCRIPTION OF THE DRAWINGS

FIGS. 1A and 1B show chimeric antigen receptor expression and selective cytotoxicity of clonal NK-92/5.28.z cells.

FIG. 1A) is a schematic representation of lentiviral transfer plasmid pS-5.28.z-W encoding under the transcriptional control of the Spleen Focus Forming Virus promoter (SFFV) the chimeric antigen receptor (CAR) 5.28.z. CAR 5.28.z consists of an immunoglobulin heavy chain signal peptide (SP), the ErbB2-specific scFv (FRP5) antibody fragment (scFv), a hinge region (CD8α), followed by transmembrane and intracellular domains of CD28 and the intracellular domain of CD3ζ. The CAR-encoding sequence is flanked by 5' and 3' long terminal repeats (LTR) of the vector (not shown).

FIG. 1B) is a graph showing CAR-expression by the clonal NK-92/5.28.z cell line generated under GMP conditions by transduction with lentiviral vector S-5.28.z-W determined by flow cytometry with ErbB2-Fc fusion protein (open area). Unmodified NK-92 cells served as control (gray area).

FIG. 2A) is a schematic representation of the integration sites of the lentiviral CAR vector S-5.28.z-W (shaded box) flanked by 5' and 3' long terminal repeat (LTR) sequences (filled boxes) in genomic DNA (open boxes). The PCR strategy to map the integration sites in the TRAF2 gene on chromosome 9 and in an intergenic region on chromosome 2 is indicated.

FIGS. 2B and 2C are images showing PCR analysis of vector integrations.

FIG. 2B) shows specific DNA sequences encompassing the junctions between the TRAF2 gene and the 5' end of the integrated CAR vector (TRAF2-CAR), and between the 3' end of the integrated CAR vector and the TRAF2 gene (CAR-TRAF2) amplified by PCR with genomic DNA from 3 different passages of NK-92/5.28.z cells as template and the indicated oligonucleotide primer pairs, yielding characteristic 587 and 503 bp amplification products. Genomic DNA of unmodified NK-92 cells as well as samples without template DNA ($H_2O$) were included as controls.

For FIG. 2C), likewise, specific DNA sequences encompassing the junctions between the intergenic region in chromosome 2 and 5' (IGCHR2-CAR) and 3' ends (CAR-IGCHR2) of the integrated CAR vector were amplified, yielding characteristic 679 and 376 bp amplification products.

M: DNA marker (GeneRuler 100 bp Plus DNA Ladder, Thermo Scientific).

Figure 3A:
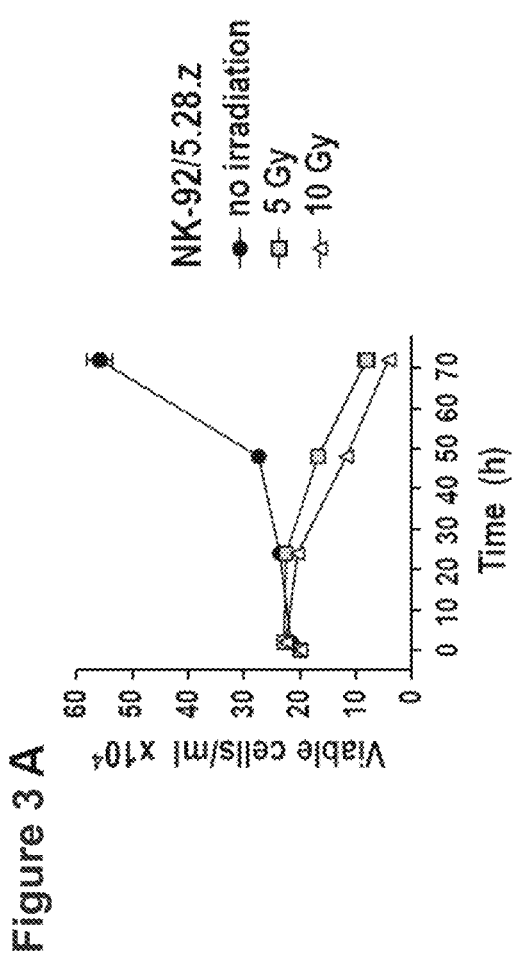
Figure 3B:
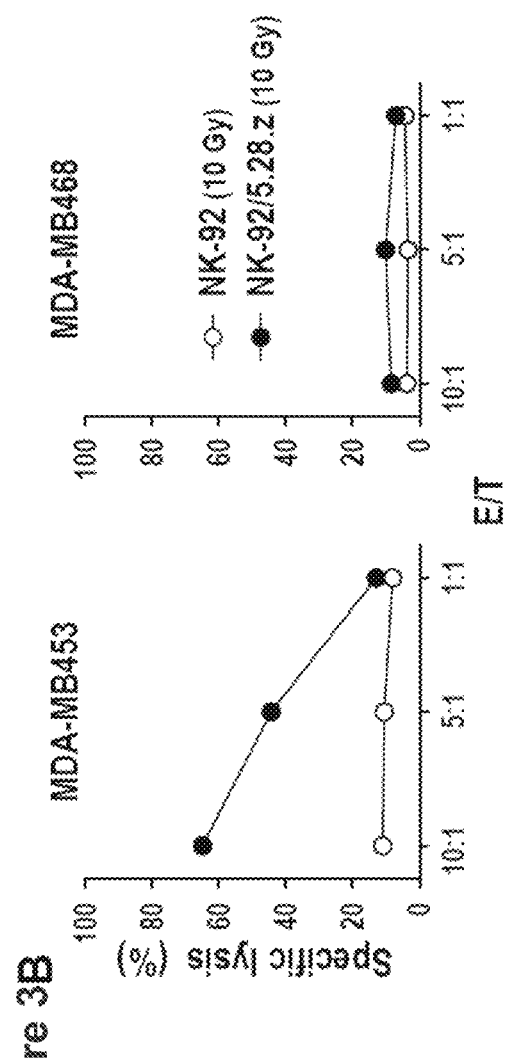

FIGS. 3A and 3B are graphs showing growth and cytotoxic activity of NK-92/5.28.z cells upon γ-irradiation.

For FIG. 3A), to investigate the effect on viability, NK-92/5.28.z cells were irradiated with 5 or 10 Gy and cultured for up to 72 hours. Proliferation was analyzed by counting viable cells at the indicated time points using trypan blue exclusion.

FIG. 3B) shows cytotoxic activity of NK-92/5.28.z cells 24 hours after irradiation with 10 Gy against ErbB2-positive MDA-MB453 and ErbB2-negative MDA-MB468 breast carcinoma cells determined in FACS-based cytotoxicity assays at different effector to target ratios (E/T) as indicated (filled circles). Unmodified NK-92 cells 24 hours after irradiation were included for comparison (open circles).

Figure 4:
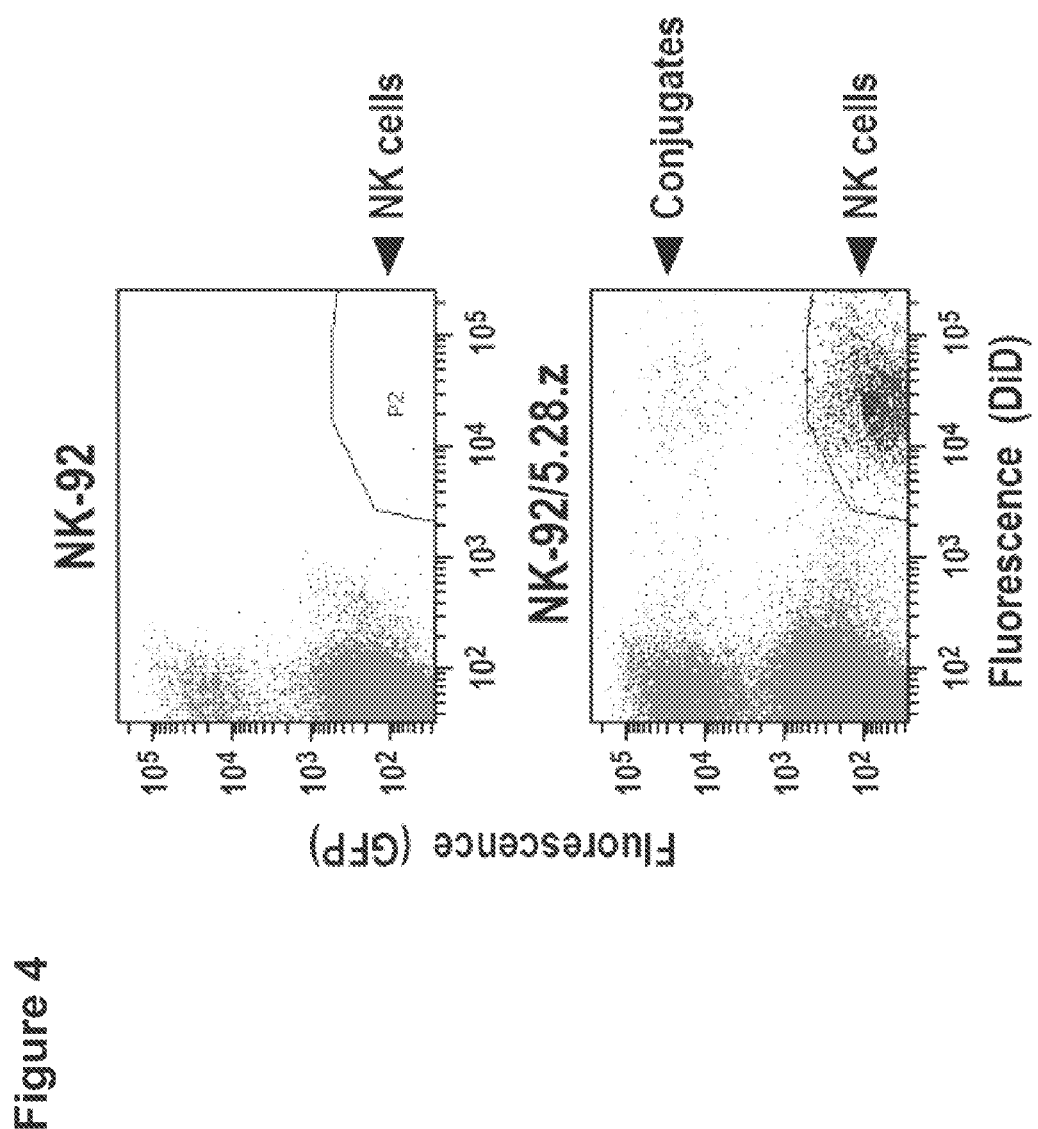

FIG. 4. Homing of NK-92/5.28.z cells to ErbB2-positive breast carcinomas in vivo.

Unmodified NK-92 (upper panel) or ErbB2-specific NK-92/5.28.z cells (lower panel) were labeled with fluorescent DiD labeling reagent and intravenously injected into NSG mice carrying established orthotopic MDA-MB453/EGFP breast carcinoma xenografts. Twenty-four hours after injection, tumors were excised, single cell suspensions were prepared, and analyzed for the presence of EGFP-expressing and DiD-labeled cells. DiD-positive NK cells are indicated in dark grey (lower right quadrants). EGFP-positive breast carcinoma cells (upper left quadrants) and double-negative murine stromal cells (lower left quadrants) are indicated in light grey. Double-positive events (upper right quadrant) represent conjugates of CAR-expressing NK-92/5.28.z and MDA-MB453/EGFP target cells. Representative flow cytometric data from one animal of each group are shown (n=3).

Figure 5B:
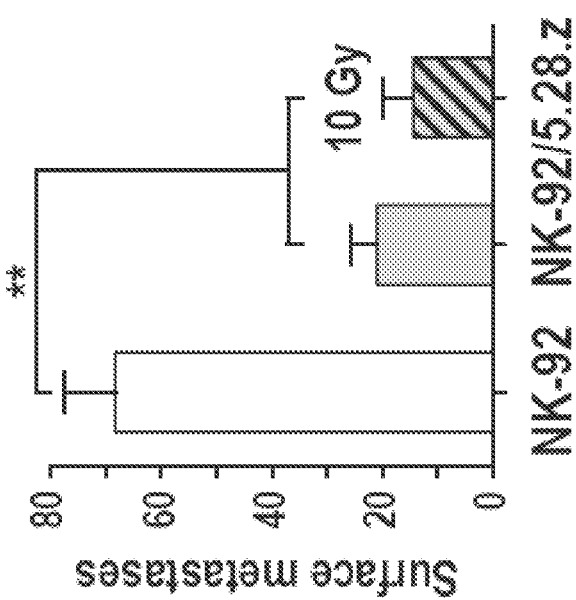
Figure 5A:
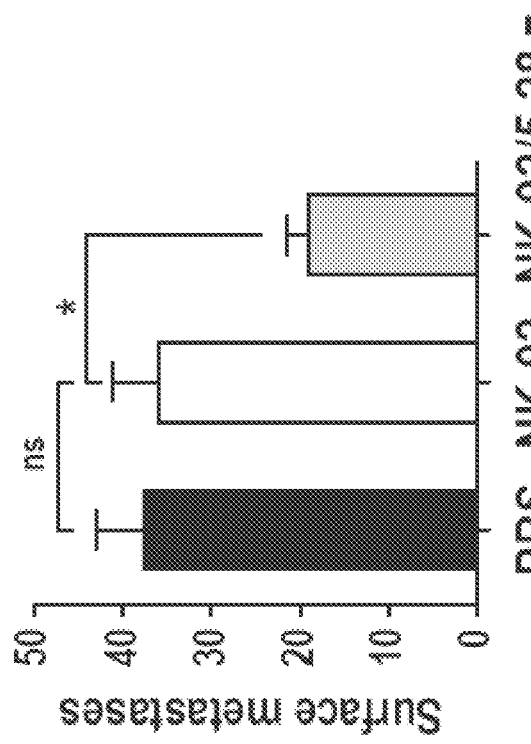

FIGS. 5A and 5B are graphs showing in vivo antitumor activity of NK-92/5.28.z cells.

For FIG. 5A), to investigate antitumor activity, NSG mice were intravenously injected with Renca-lacZ/ErbB2 renal cell carcinoma cells. Then animals were treated twice by i.v. injection of unmodified NK-92 or clonal NK-92/5.28.z cells at days 1 and 3 after tumor cell injection.

Control mice received PBS. Four weeks after tumor challenge, lungs were excised and tumor nodules on the lung surface were counted.

For FIG. 5B), in a separate experiment, NSG mice injected with Renca-lacZ/ErbB2 cells were treated as described above with non-irradiated NK-92 or NK-92/5.28.z cells, or NK-92/5.28.z cells irradiated with 10 Gy as indicated. Mean values±SEM are shown; n=5. ns, p>0.05; *, p<0.05; **, p<0.01.

EXAMPLES

Example 1

1.1 Methods
Cells and Culture Conditions
Human K562 erythroleukemia cells (ATCC, Manassas, Va.) were maintained in RPMI 1640 medium (Lonza, Köln, Germany). Human MDA-MB453 and MDA-MB468 breast carcinoma cells, and HEK 293T cells (all ATCC) were cultured in DMEM (Lonza). All media were supplemented with 10% heat-inactivated FBS, 2 mM L-glutamine, 100 U/ml penicillin, 100 µg/ml streptomycin. Human NK-92 cells (ATCC) were propagated in X-VIVO 10 medium (Lonza) supplemented with 5% heat-inactivated human plasma (German Red Cross Blood Service Baden-Württemberg—Hessen, Frankfurt, Germany) and 100 IU/ml IL-2 (Proleukin; Novartis Pharma, Nurnberg, Germany). Murine Renca-lacZ/ErbB2 and Renca-lacZ/EGFR renal cell carcinoma cells expressing human ErbB2 or EGFR were cultured in RPMI-1640 medium supplemented with 10% FBS, 2 mM L-glutamine, 100 U/ml penicillin, 100 µg/ml streptomycin, 0.25 mg/ml zeocin and 0.48 mg/ml G418 (Maurer-Gebhard et al., 1998).

Generation of CAR-Expressing NK-92/5.28.z Cells

The CAR sequence 5.28.z was designed by in silico assembly of an immunoglobulin heavy chain signal peptide, ErbB2-specific scFv(FRP5) antibody fragment and a modified CD8α hinge region (wherein an unpaired cysteine within the hinge region was replaced by serine), followed by CD28 transmembrane and intracellular domains and CD3ζ intracellular domain. A codon-optimized fusion gene was synthesized (GeneArt, Regensburg, Germany) and inserted into lentiviral transfer plasmid pHR'SIN-cPPT-WPREmut vector (Schambach et al., 2006), resulting in lentiviral transfer plasmid pS-5.28.z-W. VSV-G pseudotyped vector particles were generated and NK-92 cells were transduced as described previously (Sahm et al., 2012), and for cell clone NK-92/5.28.z confirmed by PCR analysis of genomic DNA with oligonucleotide primers that yielded characteristic PCR products spanning the junctions between chromosomal DNA and integrated vector sequences.

Cytotoxicity Assays

Cytotoxicity of NK-92 cells towards target cells was analyzed in FACS-based assays as described (Sahm et al., 2012). Briefly, target cells were labeled with calcein violet AM (Molecular Probes, Invitrogen, Karlsruhe, Germany) and co-cultured with effector cells at various effector to target (E/T) ratios for 2 h at 37° C. After co-culture, 250 µl of a 1 µg/ml propidium iodide (PI) solution were added to each sample 5 min before flow cytometric analysis in a FACSCanto II flow cytometer (BD Biosciences, Heidelberg, Germany). Data were analyzed using FACSDiva software (BD Biosciences). To calculate specific cytotoxicity, the number of spontaneously lysed target cells in the absence of effector cells was subtracted from the number of dead target cells determined as calcein violet AM and PI double positive in the measured sample.

Irradiation of NK-92 Cells

NK-92/5.28.z and unmodified NK-92 cells were collected by centrifugation, counted, washed, resuspended in fresh growth medium and irradiated with 5 or 10 Gy using a Biobeam 2000 device (Gamma Service Medical, Leipzig, Germany). For in vitro proliferation and cytotoxicity assays, irradiated cells were washed, resuspended in fresh growth medium and cultured for up to 72 h. Proliferation was analyzed by counting viable cells at different time points using trypan blue exclusion. For in vivo experiments, cells were irradiated with 10 Gy and applied directly.

Tumor Homing of NK-92 Cells

EGFP-expressing MDA-MB453 breast carcinoma cells were derived by transduction of MDA-MB453 cells with an EGFP-encoding lentiviral vector and enrichment by flow cytometric cell sorting. Orthotopic breast carcinoma xenografts were induced in 4 to 6 weeks old female NOD-SCID IL2R $\gamma^{null}$ (NSG) mice (Charles River, Sulzfeld, Germany) by injection of $5\times10^6$ MDA-MB453/EGFP cells suspended in Matrigel (BD Biosciences) into the mammary fat pad. When tumors were palpable, NK-92/5.28.z or unmodified NK-92 cells were labeled with DiD (1,1'-dioctadecyl-3,3,3', 3' tetramethylindodicarbocyanine) labeling reagent (Molecular Probes/Life Technologies, Darmstadt, Germany) as described (Tavri et al., 2009), and injected into the lateral tail vein of the tumor bearing mice ($1\times10^7$ cells/animal; 3 animals per group). Twenty-four hours after injection, mice were sacrificed, tumors were excised, single cell suspensions were prepared, and analyzed for the presence of EGFP-expressing and DiD-labeled cells in a FACSCanto II flow cytometer.

In Vivo Antitumor Activity

Four to 6 weeks old female NSG mice were injected with $1\times10^5$ Renca-lacZ/ErbB2 cells into the lateral tail vein at day 0. Then animals were treated by i.v. injection of $1\times10^7$ NK-92/5.28.z or unmodified NK-92 cells at days 1 and 3 after tumor cell injection (5 mice/group). Control mice received PBS. In separate experiments, NSG mice injected with Renca-lacZ/ErbB2 cells were also treated with irradiated NK-92/5.28.z cells (10 Gy), or non-irradiated NK-92/5.28.z and unmodified NK-92 cells as controls (5 mice/group). Four weeks after tumor challenge, all animals were sacrificed, lungs were excised, and tumor nodules on the lung surface were counted as described (Maurer-Gebhard et al., 1998).

Statistical Analysis

Differences between values were evaluated using the two-tailed unpaired Student's t test. P values <0.05 were considered significant. Statistical calculations were performed using Prism 5 software (GraphPad Software, La Jolla, Calif.).

1.2 Results

Generation of an ErbB2-Specific NK-92/5.28.z Single Cell Clone

Figure 1C:
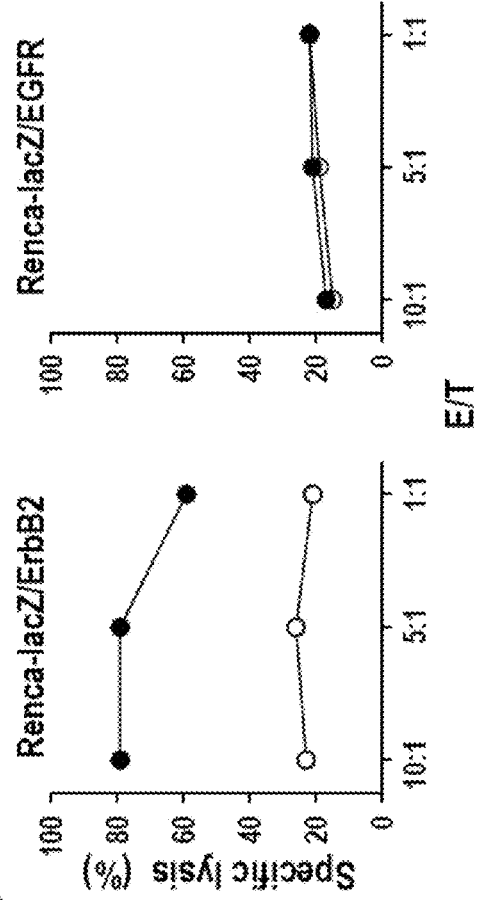
FIG. 1C) are graphs showing specific cell killing by NK-92/5.28.z cells (filled circles) in FACS-based cytotoxicity assays at different effector to target ratios (E/T) using murine renal cell carcinoma cells as targets that stably express human ErbB2 (Renca-lacZ/ErbB2) or human EGFR (Renca-lacZ/EGFR) as a control. Unmodified NK-92 cells were included for comparison (open circles).

The chimeric antigen receptor 5.28.z was used to generate a clinically applicable ErbB2-specific NK-92 cell line (FIG. 1A). VSV-G pseudotyped lentiviral CAR vector particles were produced and NK-92 cells from a certified NK-92 master cell bank (Arai et al., 2008) were transduced. Single cell clones were derived by limiting dilution, and CAR-expressing cells were identified by flow cytometric analysis with ErbB2-Fc fusion protein. A total of 15 CAR-expressing single cell clones were functionally and molecularly characterized, which harbored between one and four vector copies. One cell clone termed NK-92/5.28.z which displayed high and stable CAR-expression during continuous culture in a setting reflecting large-scale expansion under GMP conditions was selected for further analysis (FIG. 1B). Selective cytotoxic activity of the retargeted cells was evaluated using Renca-lacZ/ErbB2 murine renal cell carcinoma cells stably expressing human ErbB2. Clonal NK-92/5.28.z cells displayed high cytotoxicity towards these ErbB2-expressing target cells, which were resistant to unmodified NK-92 (FIG. 1C, left panel). In contrast, ErbB2-negative negative but otherwise isogenic Renca-lacZ/EGFR cells expressing epidermal growth factor receptor displayed no enhanced sensitivity to the effector cells (FIG. 1C, right panel). This indicates that cell killing was indeed mediated by interaction of CAR 5.28.z with its target antigen ErbB2.

Figure 1D:
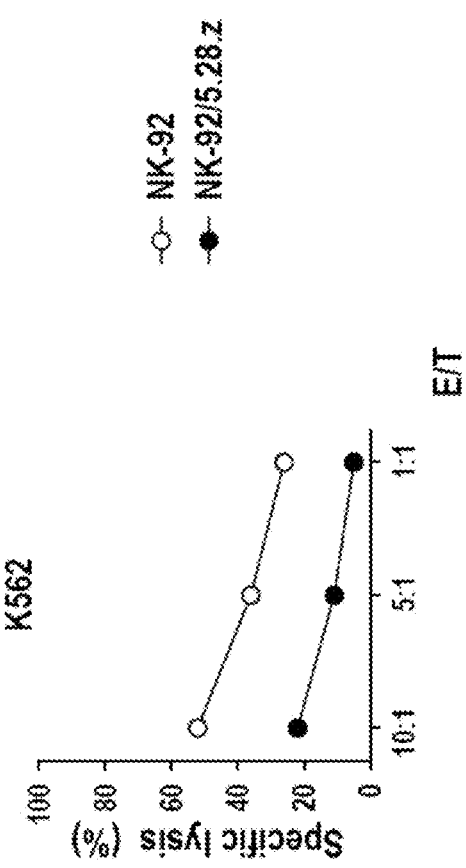
FIG. 1D) is a graph showing natural cytotoxicity of NK-92/5.28.z cells against NK-sensitive but ErbB2-negative targets compared to unmodified NK-92 cells using human K562 erythroleukemia cells as targets.

Endogenous, CAR-independent cytotoxicity of NK-92/5.28.z cells was investigated using ErbB2-negative but NK-sensitive K562 human erythroleukemia cells as targets. While K562 cells were highly sensitive to CAR-negative unmodified NK-92 cells, they were killed to a much lower extent by ErbB2-specific NK-92/5.28.z cells (FIG. 1D).

Taken together, these data demonstrate that NK-92/5.28.z cells are highly selective and efficiently kill ErbB2-expressing tumor cells, while their endogenous cytotoxicity to ErbB2-negative targets is markedly reduced when compared to unmodified NK-92 cells.

Molecular Characterization of ErbB2-Specific NK-92/5.28.z Cells

Figure 2A:
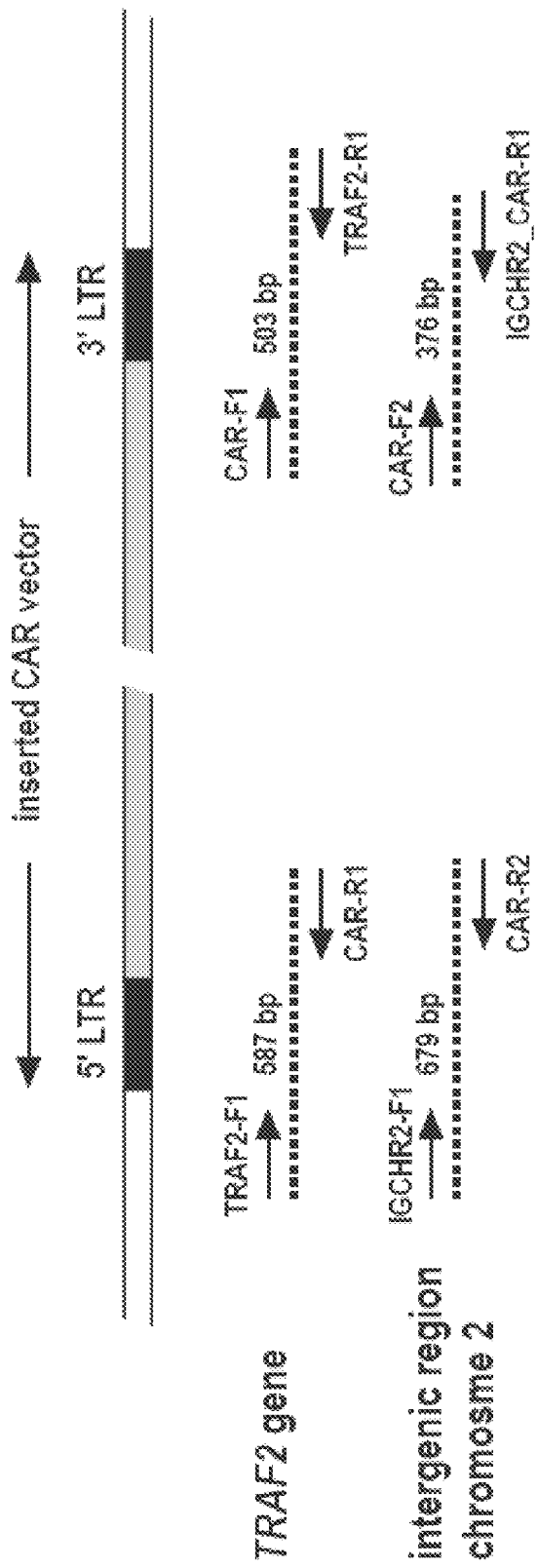
FIGS. 2A, 2B and 2C are graphs showing molecular characterization of clonal NK-92/5.28.z cells.
Figure 2:
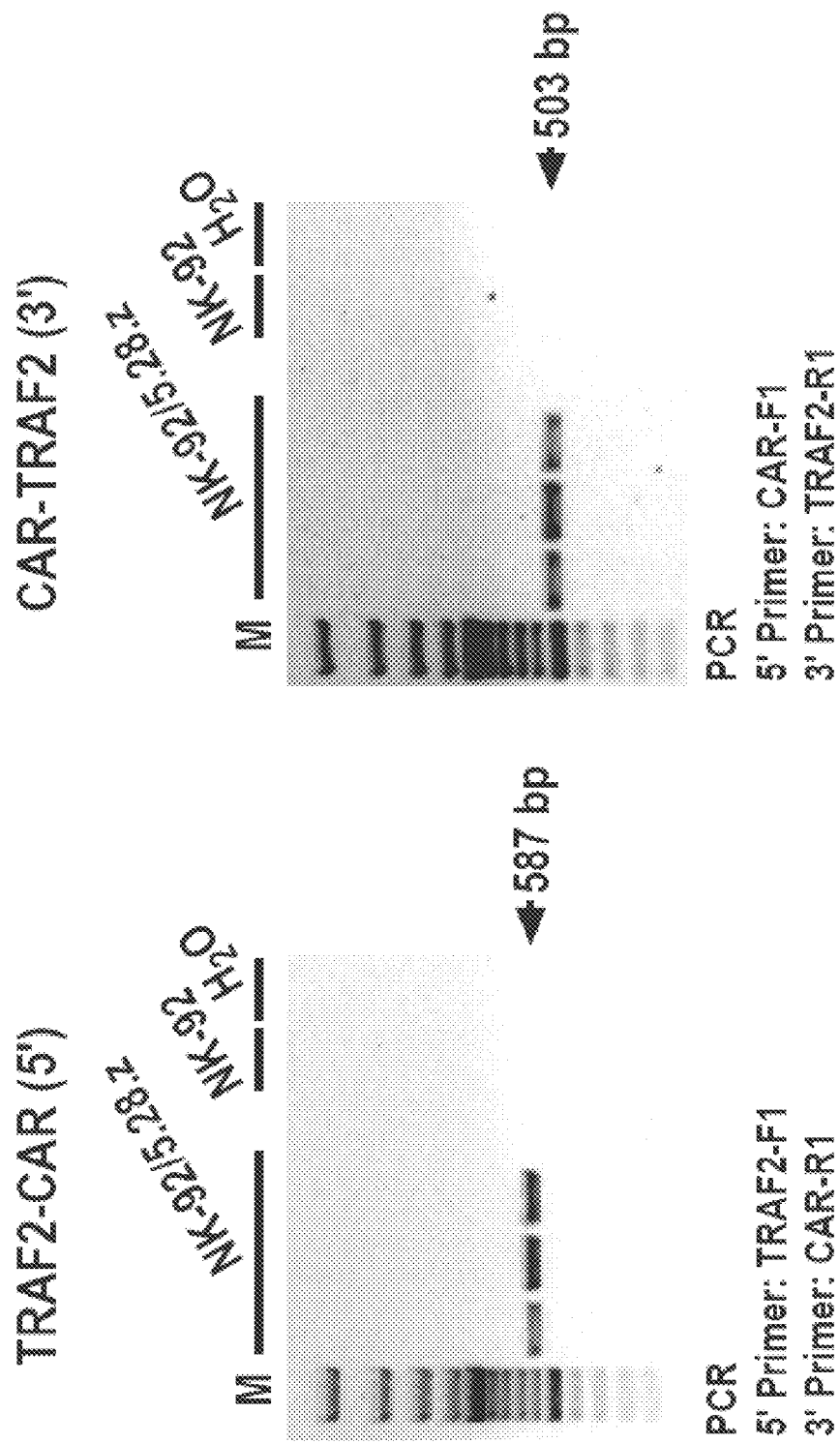
Figure 2:
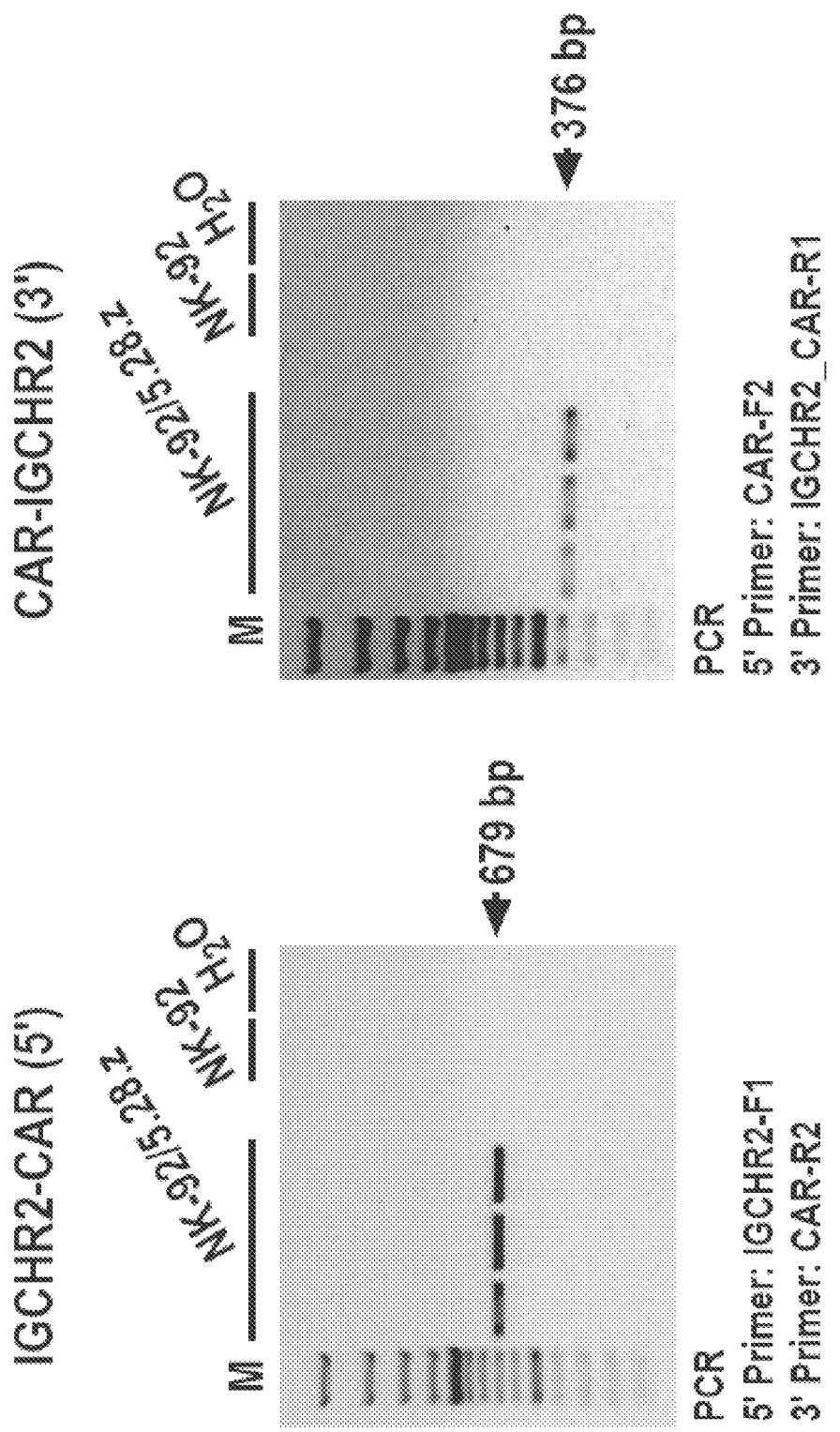

Linear amplification-mediated PCR (LAM-PCR) and DNA sequencing revealed one vector integration each in an intergenic region on chromosome 2, and in the TRAF2 gene on chromosome 9 of clonal NK-92/5.28.z cells (FIG. 2A). The integration sites were confirmed by PCR analysis of genomic DNA of NK-92/5.28.z cells from three different passages during continuous culture over several months, thereby amplifying specific DNA sequences that encompass the junctions between the TRAF2 gene and the 5' end of the integrated CAR vector, and between the 3' end of the integrated CAR vector and the TRAF2 gene (FIG. 2B, upper panels), as well as specific DNA sequences that encompass the junctions between the intergenic region in chromosome 2 and 5' and 3' ends of the integrated CAR vector (FIG. 2B, lower panels). In each case, genomic DNA of the different passages of NK-92/5.28.z cells yielded the same characteristic amplification products of defined length and sequence, demonstrating long-term stability of the vector integrations. No amplification products were obtained with the same oligonucleotide primers upon PCR analysis of genomic DNA from unmodified NK-92 cells, indicating that specific PCR analysis of the CAR vector integrations also represents a powerful diagnostic tool to molecularly identify the NK-92/5.28.z cell clone.

a) Amplification product TRAF2-CAR (5')
CAR vector integration in TRAF2 gene
5' part of vector integration
PCR product TRAF2-CAR (5') from genomic DNA of NK-92/5-28.z cells
Primers:

```
TRAF2-F1:                                    [SEQ ID NO. 1]
CTTCAGCAGGGACCAGAAACAA

CAR-R1:                                      [SEQ ID NO. 2]
CCGCTTAATACTGACGCTCTCG
``` lower case letters: TRAF2 gene
upper case letters: vector sequence
Length: 587 nucleotides

```
                                                    SEQ ID NO. 9
cttcagcagggaccagaaacaaaactcacactctttcttctctgagttga        50 gactggaaaaatgaaagattgttttaggggaaacttgagggaacagtctg       100 ggcagcctgcagggcatggccctgttcctccagggctgggaaagtcagca       150 ctgctttctggtggcgaACTGGAAGGGCTAATTCACTCCCAACGAAGACA       200

AGATCTGCTTTTTGCTTGTACTGGGTCTCTCTGGTTAGACCAGATCTGAG       250

CCTGGGAGCTCTCTGGCTAACTAGGGAACCCACTGCTTAAGCCTCAATAA       300

AGCTTGCCTTGAGTGCTTCAAGTAGTGTGTGCCCGTCTGTTGTGTGACTC       350

TGGTAACTAGAGATCCCTCAGACCCTTTTAGTCAGTGTGGAAAATCTCTA       400

GCAGTGGCGCCCGAACAGGGACTTGAAAGCGAAAGGGAAACCAGAGGAGC       450

TCTCTCGACGCAGGACTCGGCTTGCTGAAGCGCGCACGGCAAGAGGCGAG       500

GGGCGGCGACTGGTGAGTACGCCAAAAATTTTGACTAGCGGAGGCTAGAA       550

GGAGAGAGATGGGTGCGAGAGCGTCAGTATTAAGCGG                    587
``` b) Amplification product CAR-TRAF2 (3')
CAR vector integration in TRAF2 gene
3' part of vector integration
PCR product CAR-TRAF2 (3') from genomic DNA of NK-92/5-28.z cells
Primers:

```
CAR-F1:                                      [SEQ ID NO. 3]
ATCGCCACGGCAGAACTCA

TRAF2-R1:                                    [SEQ ID NO. 4]
GACCCTTCACCCAACGCTTAG
``` lower case letters: TRAF2 gene
upper case letters: vector sequence
Length: 503 nucleotides

```
                                                   SEQ ID NO. 10
ATCGCCACGGCAGAACTCATCGCCGCCTGCCTTGCCCGCTGCTGGACAGG        50

GGCTAGGTTGCTGGGCACTGATAATTCCGTGGTGTTGTCGAATTCGATAC       100

TCGAGGTCGAGGCAATTCGAGCTCGGTACCTTTAAGACCAATGACTTACA       150

AGGCAGCTGTAGATCTTAGCCACTTTTTAAAAGAAAAGGGGGACTGGAA        200
```

```
GGGCTAATTCACTCCCAACGAAGACAAGATCTGCTTTTTGCTTGTACTGG      250

GTCTCTCTGGTTAGACCAGATCTGAGCCTGGGAGCTCTCTGGCTAACTAG      300

GGAACCCACTGCTTAAGCCTCAATAAAGCTTGCCTTGAGTGCTTCAAGTA      350

GTGTGTGCCCGTCTGTTGTGTGACTCTGGTAACTAGAGATCCCTCAGACC      400

CTTTTAGTCAGTGTGGAAAATCTCTAGCAccttccctctgcagctgctgg      450 ctcagccgattgtatatgctgggagctctgcactaagcgttgggtgaagg      500 gtc                                                    503
``` c) Amplification product IGCHR2-CAR (5')
CAR vector integration in intergenic region of chromosome 2
5' part of vector integration
PCR product IGCHR2-CAR (5') from genomic DNA of NK-92/5-28.z cells
Primers:

```
        IGCHR2-F1:
                                [SEQ ID NO. 5]
        TCAGTGGAATGGGCAGCTTCAAGT

CAR-R2:
                                [SEQ ID NO. 6]
        TTCAGCAAGCCGAGTCCTGCGT
``` lower case letters: intergenic region chromosome 2
upper case letters: vector sequence
Length: 679 nucleotides

```
                                                  SEQ ID NO. 11
tcagtggaatgggcagcttcaagttgatgtcatttcaatagtaacttatt       50 tcagtctacatacttcccaagaatgcaccatctctttttatgtatttat       100 tattttgagaaagagtctcactctgtcgcccaggctggagtgcaatggca      150 tgatcttggctcactgtaacctccgtctcctgggttcaagccattctcct      200 gtctcagcctcccgggtagtggggttataggcacacaccaccacgcccgg      250 ctaattttgtattttagtaaagatggggtttcaccatgttggccaggc       300 tgggctcaaactcttgacttcaggtgatccgcccaccttggcctcccaaa      350 gtgctgggatgacaggcACTGGAAGGGCTAATTCACTCCCAACGAAGACA      400

AGATCTGCTTTTTGCTTGTACTGGGTCTCTCTGGTTAGACCAGATCTGAG      450

CCTGGGAGCTCTCTGGCTAACTAGGGAACCCACTGCTTAAGCCTCAATAA      500

AGCTTGCCTTGAGTGCTTCAAGTAGTGTGTGCCCGTCTGTTGTGTGACTC      550

TGGTAACTAGAGATCCCTCAGACCCTTTTAGTCAGTGTGGAAAATCTCTA      600

GCAGTGGCGCCCGAACAGGGACTTGAAAGCGAAAGGGAAACCAGAGGAGC      650

TCTCTCGACGCAGGACTCGGCTTGCTGAA                          679
``` d) Amplification product CAR-IGCHR2 (3')
CAR vector integration in intergenic region of chromosome 2
3' part of vector integration
PCR product CAR-IGCHR2 (3') from genomic DNA of NK-92/5-28.z cells
Primers:

CAR-F2:
ACTGATAATTCCGTGGTGTTGT   [SEQ ID NO. 7]

IGCHR2_CAR-R1:
CACTGTGGCTCAC<u>TGCTAGA</u>   [SEQ ID NO. 8]

lower case letters: intergenic region chromosome 2
upper case letters: vector sequence
Length: 376 nucleotides

```
                                                          SEQ ID NO. 12
ACTGATAATTCCGTGGTGTTGTCGAATTCGATACTCGAGGTCGAGGCAAT         50

TCGAGCTCGGTACCTTTAAGACCAATGACTTACAAGGCAGCTGTAGATCT        100

TAGCCACTTTTTAAAAGAAAAGGGGGACTGGAAGGGCTAATTCACTCCC         150

AACGAAGACAAGATCTGCTTTTTGCTTGTACTGGGTCTCTCTGGTTAGAC        200

CAGATCTGAGCCTGGGAGCTCTCTGGCTAACTAGGGAACCCACTGCTTAA        250

GCCTCAATAAAGCTTGCCTTGAGTGCTTCAAGTAGTGTGTGCCCGTCTGT        300

TGTGTGACTCTGGTAACTAGAGATCCCTCAGACCCTTTTAGTCAGTGTGG        350

AAAATCTCTAGCAgtgagccacagtg                                376
```

Target Cell Killing by Irradiated NK-92/5.28.z Cells

In phase I clinical trials with unmodified NK-92, irradiation of cells with 10 Gy prior to infusion had been included as a safety measure to prevent permanent engraftment (Arai et al., 2008; Tonn et al., 2013). Similar safety measures may be important for clinical use of retargeted NK-92 cells. Hence, we tested the effects of γ-irradiation on growth and cytotoxic activity of clonal NK-92/5.28.z cells. Irradiation with 5 Gy was sufficient to prevent further replication, while the number of viable NK-92/5.28.z cells remained almost constant for 24 hours after exposure to 5 or 10 Gy before declining gradually (FIG. 3A). To assess effects on cytotoxic activity, NK-92/5.28.z cells irradiated with 10 Gy were cultured for 24 hours and then co-incubated for two hours with ErbB2-expressing human MDA-MB453 breast carcinoma cells as targets. Irradiated NK-92/5.28.z displayed high and specific cytotoxicity towards MDA-MB453 cells (65% specific lysis at an E/T ratio of 10:1), while they did not lyse ErbB2-negative human MDA-MB468 breast carcinoma cells (FIG. 3B). Neither MDA-MB453 nor MDA-MB468 cells were killed by irradiated unmodified NK-92 cells.

Homing of NK-92/5.28.z Cells to ErbB2-Positive Breast Carcinomas

The potential of NK-92/5.28.z cells to home to established tumors was investigated in an orthotopic breast carcinoma model. MDA-MB453 cells transduced with an EGFP-encoding lentiviral vector were implanted into the mammary fat pad of female NSG mice, and allowed to grow until tumors were palpable. Then NK-92/5.28.z and unmodified NK-92 cells were labeled with fluorescent DiD labeling reagent, and intravenously injected into the tumor-bearing animals. Twenty-four hours later, tumors were excised, single cell suspensions were prepared, and analyzed for the presence of EGFP-expressing tumor cells and DiD-labeled NK cells. In mice injected with unmodified NK-92, only a few of the NK cells were found in the tumors (FIG. 4, upper panel). In contrast, NK-92/5.28.z cells were strongly enriched in MDA-MB453/EGFP xenografts (FIG. 4, lower panel). Importantly, we also found conjugates of NK-92/5.28.z and MDA-MB453/EGFP cells in the cell suspensions prepared from the tumors. These data demonstrate that NK-92/5.28.z cells retain target cell specificity in vivo, and are capable of penetrating tissues and homing to distant tumor sites.

In Vivo Antitumor Activity of NK-92/5.28.z Cells

For evaluation of in vivo antitumor activity we chose an experimental lung metastasis model. NSG mice received intravenous injections of Renca-lacZ/ErbB2 cells, followed by i.v. injections of unmodified NK-92 or retargeted NK-92/5.28.z cells at days 1 and 3 after tumor cell inoculation. Control mice received PBS. Four weeks after tumor challenge, lungs were excised and tumor nodules on the lung surface were counted. While treatment with unmodified NK-92 cells did not affect metastasis formation in comparison to PBS-treated controls, retargeted NK-92/5.28.z cells reduced the number of pulmonary tumor nodules in this experiment by approximately 50% (mean number of lung surface metastases: PBS: 37.7±5.4; NK-92: 36±5.1; NK-92/5.28.z: 19±2.6; p<0.05) (FIG. 5A). To assess whether NK-92/5.28.z cells retain in vivo antitumor activity after γ-irradiation, a similar experiment was performed employing NK-92/5.28.z cells that were irradiated with 10 Gy prior to injection. Control animals were treated with non-irradiated NK-92/5.28.z or non-irradiated unmodified NK-92 cells. In comparison to treatment with unmodified NK-92 cells, both, non-irradiated and irradiated NK-92/5.28.z cells markedly reduced the number of pulmonary tumor nodules (mean number of lung surface metastases: NK-92: 68.3±9.1; NK-92/5.28.z: 21±4.9; irradiated NK-92/5.28.z: 14.4±5.5; p<0.01) (FIG. 5B). These data demonstrate specific antitumor activity of systemically applied NK-92/5.28.z cells against ErbB2-expressing tumor cells in a model reflecting disseminated disease. Importantly, viability and functionality of NK-92/5.28.z cells were transiently preserved after γ-irradiation at a dose that prevents further effector cell replication, permitting target cell recognition and killing in vivo.

REFERENCES

Arai S, Meagher R, Swearingen M, et al. Infusion of the allogeneic cell line NK-92 in patients with advanced renal cell cancer or melanoma: a phase I trial. *Cytotherapy.* 2008; 10(6):625-632.

Boissel L, Betancur M, Wels W S, et al. Transfection with mRNA for CD19 specific chimeric antigen receptor restores NK cell mediated killing of CLL cells. *Leuk Res.* 2009; 33(9):1255-1259.

Geller M A, Miller J S. Use of allogeneic NK cells for cancer immunotherapy. *Immunotherapy* 2011; 3:1445-1459.

Gong et al., Characterization of a human cell line (NK-92) with phenotypical and functional characteristics of activated natural killer cells. *Leukemia*. 1994 April; 8(4):652-8.

Grupp S A, Kalos M, Barrett D, et al. Chimeric antigen receptor-modified T cells for acute lymphoid leukemia. *N Engl J Med*. 2013; 368(16):1509-1518.

Hynes N E, Lane H A. ERBB receptors and cancer: the complexity of targeted inhibitors. *Nat Rev Cancer*. 2005; 5(5):341-354.

Kalos M, June C H. Adoptive T cell transfer for cancer immunotherapy in the era of synthetic biology. *Immunity*. 2013; 39(1):49-60.

Koch J, Steinle A, Watzl C, et al. Activating natural cytotoxicity receptors of natural killer cells in cancer and infection. *Trends Immunol*. 2013; 34(4):182-191.

Maurer-Gebhard M, Schmidt M, Azemar M, et al. Systemic treatment with a recombinant erbB-2 receptor-specific tumor toxin efficiently reduces pulmonary metastases in mice injected with genetically modified carcinoma cells. *Cancer Res*. 1998; 58(12):2661-2666.

Müller T, Uherek C, Maki G, et al. Expression of a CD20-specific chimeric antigen receptor enhances cytotoxic activity of NK cells and overcomes NK-resistance of lymphoma and leukemia cells. *Cancer Immunol Immunother*. 2008; 57(3): 411-423.

Sahm C, Schönfeld K, Wels W S. Expression of IL-15 in NK cells results in rapid enrichment and selective cytotoxicity of gene-modified effectors that carry a tumor-specific antigen receptor. *Cancer Immunol Immunother*. 2012; 61(9): 1451-1461.

Schambach A, Bohne J, Baum C, et al. Woodchuck hepatitis virus post-transcriptional regulatory element deleted from X protein and promoter sequences enhances retroviral vector titer and expression. *Gene Ther*. 2006; 13 (7):641-645.

Schmidt M, Carbonaro D A, Speckmann C, et al. Clonality analysis after retroviral-mediated gene transfer to CD34+ cells from the cord blood of ADA-deficient SCID neonates. *Nat Med*. 2003; 9(4):463-468.

Tavri S, Jha P, Meier R, et al. Optical imaging of cellular immunotherapy against prostate cancer. *Mol Imaging*. 2009; 8(1):15-26.

Tonn T, Schwabe D, Klingemann H G, et al. Treatment of patients with advanced cancer with the natural killer cell line NK-92. *Cytotherapy*. 2013; 15(12):1563-1570.

---

The invention claimed is:

1. A method of treating cancer in a subject comprising administering to the subject a therapeutically effective amount of ErbB2-specific NK-92 cells, the cells containing a genomically integrated lentiviral vector encoding a chimeric antigen receptor comprising an ErbB2-specific scFv antibody fragment, a hinge region, transmembrane and intracellular domains of CD28, and intracellular domain of CD3 zeta, wherein the cells are NK-92/5.28.z cells having accession number DSM ACC3244, and wherein administration treats the cancer in the subject.

2. The method of claim 1, wherein said vector is genomically integrated (i) in an intergenic region on chromosome 2, and (ii) in the TRAF2 gene on chromosome 9.

3. The method of claim 1, wherein the cell or cell line is characterized in that by PCR analysis of the genomic DNA of said cell or cell line at least one of the following amplification products is obtained:
   PCR with primers of SEQ ID NOs. 1 and 2 yields an amplification product with the nucleotide sequence of SEQ ID NO. 9;
   PCR with primers of SEQ ID NOs. 3 and 4 yields an amplification product with the nucleotide sequence of SEQ ID NO. 10;
   PCR with primers of SEQ ID NOs. 5 and 6 yields an amplification product with the nucleotide sequence of SEQ ID NO. 11;
   PCR with primers of SEQ ID NOs. 7 and 8 yields an amplification product with the nucleotide sequence of SEQ ID NO. 12.

4. The method of claim 1, wherein the cells show reduced or no natural cytotoxicity to ErbB2-negative cells.

5. The method of claim 1, wherein the cells show increased cytotoxicity to ErbB2-expressing tumor cells compared to unmodified NK-92 cells.

6. The method of claim 1, wherein the ErbB2-specific scFv antibody fragment comprises the amino acid sequence of SEQ ID NO. 13.

7. The method of claim 1, wherein the ErbB2-specific scFv antibody fragment is encoded by the nucleotide sequence of SEQ ID NO. 14.

8. The method of claim 1, wherein the chimeric antigen receptor comprises the amino acid sequence of SEQ ID NO. 15.

9. The method of claim 1, wherein the chimeric antigen receptor is encoded by the nucleotide sequence of SEQ ID NO. 16.

10. The method of claim 1, wherein the cancer is an ErbB2-expressing cancer.

11. The method of claim 1, wherein the cancer is selected from the group consisting of breast cancer, ovarian cancer, gastric cancer, prostate cancer, squamous cell carcinoma, head and neck cancer, colon cancer, pancreatic cancer, uterine cancer, renal cell cancer, glioblastoma, medulloblastoma, sarcoma, and lung cancer.

12. The method of claim 1, wherein the method comprises pre-treatment of the cells by irradiation.

13. The method of claim 1, wherein $1 \times 10^5$ to $1 \times 10^7$ cells are administered to the subject.

14. The method of claim 1, wherein the cells are administered intravenously.

15. The method of claim 12, wherein the irradiation is γ-irradiation.

* * * * *

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cttcagcagg gaccagaaac aa                                                  22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ccgcttaata ctgacgctct cg                                                  22

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
atcgccacgg cagaactca                                                      19

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gacccttcac ccaacgctta g                                                   21
```

```
<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tcagtggaat gggcagcttc aagt                                          24

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ttcagcaagc cgagtcctgc gt                                            22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
actgataatt ccgtggtgtt gt                                            22

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cactgtggct cactgctaga                                               20

<210> SEQ ID NO 9
<211> LENGTH: 587
<212> TYPE: DNA
<213> ORGANISM: Artificial Sequence
<220> FEATURE:
<223> OTHER INFORMATION: Amplification product of CAR vector integration
      in TRAF2 gene

<400> SEQUENCE: 9
cttcagcagg gaccagaaac aaaactcaca ctctttcttc tctgagttga gactggaaaa    60
atgaaagatt gttttagggg aaacttgagg gaacagtctg ggcagcctgc agggcatggc   120
cctgttcctc cagggctggg aaagtcagca ctgctttctg gtggcgaact ggaagggcta   180
attcactccc aacgaagaca agatctgctt tttgcttgta ctgggtctct ctggttagac   240
cagatctgag cctgggagct ctctggctaa ctagggaacc cactgcttaa gcctcaataa   300
agcttgcctt gagtgcttca agtagtgtgt gcccgtctgt tgtgtgactc tggtaactag   360
agatccctca gaccctttta gtcagtgtgg aaaatctcta gcagtggcgc ccgaacaggg   420
acttgaaagc gaaagggaaa ccagaggagc tctctcgacg caggactcgg cttgctgaag   480
cgcgcacggc aagaggcgag gggcggcgac tggtgagtac gccaaaaatt ttgactagcg   540
gaggctagaa ggagagagat gggtgcgaga gcgtcagtat taagcgg               587
```

<210> SEQ ID NO 10
<211> LENGTH: 503
<212> TYPE: DNA
<213> ORGANISM: Artificial Sequence
<220> FEATURE:
<223> OTHER INFORMATION: Amplification product of CAR vector integration in TRAF2 gene

<400> SEQUENCE: 10

```
atcgccacgg cagaactcat cgccgcctgc cttgcccgct gctggacagg ggctaggttg      60
ctgggcactg ataattccgt ggtgttgtcg aattcgatac tcgaggtcga ggcaattcga     120
gctcggtacc tttaagacca atgacttaca aggcagctgt agatcttagc cacttttaa      180
aagaaaaggg gggactggaa gggctaattc actcccaacg aagacaagat ctgctttttg     240
cttgtactgg gtctctctgg ttagaccaga tctgagcctg ggagctctct ggctaactag     300
ggaacccact gcttaagcct caataaagct tgccttgagt gcttcaagta gtgtgtgccc     360
gtctgttgtg tgactctggt aactagagat ccctcagacc cttttagtca gtgtggaaaa     420
tctctagcac cttccctctg cagctgctgg ctcagccgat tgtatatgct gggagctctg     480
cactaagcgt tgggtgaagg gtc                                             503
```

<210> SEQ ID NO 11
<211> LENGTH: 679
<212> TYPE: DNA
<213> ORGANISM: Artificial Sequence
<220> FEATURE:
<223> OTHER INFORMATION: Amplification product of CAR vector integration in intergenic region of chromosome 2

<400> SEQUENCE: 11

```
tcagtggaat gggcagcttc aagttgatgt catttcaata gtaacttatt tcagtctaca      60
tacttcccaa gaatgcacca tctcttttt atgtatttat tattttgaga aagagtctca     120
ctctgtcgcc caggctggag tgcaatggca tgatcttggc tcactgtaac ctccgtctcc     180
tgggttcaag ccattctcct gtctcagcct cccgggtagt ggggttatag gcacacacca     240
ccacgcccgg ctaatttttg tatttttagt aaagatgggg tttcaccatg ttggccaggc     300
tgggctcaaa ctcttgactt caggtgatcc gcccaccttg gcctcccaaa gtgctgggat     360
gacaggcact ggaagggcta attcactccc aacgaagaca agatctgctt tttgcttgta     420
ctgggtctct ctggttagac cagatctgag cctgggagct ctctggctaa ctagggaacc     480
cactgcttaa gcctcaataa agcttgcctt gagtgcttca agtagtgtgt gcccgtctgt     540
tgtgtgactc tggtaactag agatccctca gaccctttta gtcagtgtgg aaaatctcta     600
gcagtggcgc ccgaacaggg acttgaaagc gaaagggaaa ccagaggagc tctctcgacg     660
caggactcgg cttgctgaa                                                  679
```

<210> SEQ ID NO 12
<211> LENGTH: 376
<212> TYPE: DNA
<213> ORGANISM: Artificial Sequence
<220> FEATURE:
<223> OTHER INFORMATION: Amplification product of CAR vector integration in intergenic region of chromosome 2

<400> SEQUENCE: 12

```
actgataatt ccgtggtgtt gtcgaattcg atactcgagg tcgaggcaat tcgagctcgg      60
tacctttaag accaatgact tacaaggcag ctgtagatct tagccacttt ttaaaagaaa     120
```

```
aggggggact ggaagggcta attcactccc aacgaagaca agatctgctt tttgcttgta    180
ctgggtctct ctggttagac cagatctgag cctgggagct ctctggctaa ctagggaacc    240
cactgcttaa gcctcaataa agcttgcctt gagtgcttca agtagtgtgt gcccgtctgt    300
tgtgtgactc tggtaactag agatccctca gaccttttta gtcagtgtgg aaaatctcta    360
gcagtgagcc acagtg    376
```

<210> SEQ ID NO 13
<211> LENGTH: 241
<212> TYPE: PRT
<213> ORGANISM: Artificial Sequence
<220> FEATURE:
<223> OTHER INFORMATION: ErbB2-specific scFv antibody fragment FRP5

<400> SEQUENCE: 13

```
Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Ser Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Leu Thr Gln Ser His Lys Phe
    130                 135                 140

Leu Ser Thr Ser Val Gly Asp Arg Val Ser Ile Thr Cys Lys Ala Ser
145                 150                 155                 160

Gln Asp Val Tyr Asn Ala Val Ala Trp Tyr Gln Gln Lys Pro Gly Gln
                165                 170                 175

Ser Pro Lys Leu Leu Ile Tyr Ser Ala Ser Ser Arg Tyr Thr Gly Val
            180                 185                 190

Pro Ser Arg Phe Thr Gly Ser Gly Ser Gly Pro Asp Phe Thr Phe Thr
        195                 200                 205

Ile Ser Ser Val Gln Ala Glu Asp Leu Ala Val Tyr Phe Cys Gln Gln
    210                 215                 220

His Phe Arg Thr Pro Phe Thr Phe Gly Ser Gly Thr Lys Leu Glu Ile
225                 230                 235                 240

Lys
```

<210> SEQ ID NO 14
<211> LENGTH: 723
<212> TYPE: DNA
<213> ORGANISM: Artificial Sequence
<220> FEATURE:
<223> OTHER INFORMATION: Nucleotide sequence encoding ErbB2-specific
      scFv antibody fragment FRP5

<400> SEQUENCE: 14

```
caggtgcagc tgcagcagag cggccctgag ctgaagaagc ccggcgagac agtcaagatc    60
```

```
agctgcaagg ccagcggcta ccccttcacc aactacggca tgaactgggt gaaacaggcc    120
ccaggccagg gactgaagtg gatgggctgg atcaacacca gcaccggcga gagccacttc    180
gccgacgact tcaagggcag attcgacttc agcctggaaa ccagcgccaa caccgcctac    240
ctgcagatca caaacctgaa gagcgaggac agcgccacct actttgcgc cagatgggag     300 gtgtaccacg gctacgtgcc ctactggggc cagggcacca ccgtgaccgt gtccagcggc    360
ggagggggct ctggcggcgg aggatctggg gagggggca gcgacatcca gctgacccag     420
agccacaagt tctgagcac cagcgtgggc gaccgggtgt ccatcacctg caaagccagc     480
caggacgtgt acaacgccgt ggcctggtat cagcagaagc tggccagag ccccaagctg     540 ctgatctaca gcgccagcag ccggtacacc ggcgtgccca gcaggttcac cggcagcggc    600
agcggcccag acttcacctt caccatcagc agcgtgcagg ccgaggacct ggccgtgtac    660
ttctgccagc agcacttccg gaccccttc accttcggct ccggcaccaa gctggaaatc     720
aag                                                                  723
```

<210> SEQ ID NO 15
<211> LENGTH: 504
<212> TYPE: PRT
<213> ORGANISM: Artificial Sequence
<220> FEATURE:
<223> OTHER INFORMATION: ErbB2-specific chimeric antigen receptor

<400> SEQUENCE: 15

```
Met Asp Trp Ile Trp Arg Ile Leu Phe Leu Val Gly Ala Ala Thr Gly
1               5                   10                  15

Ala His Ser Gln Val Gln Leu Gln Gln Ser Gly Pro Glu Leu Lys Lys
            20                  25                  30

Pro Gly Glu Thr Val Lys Ile Ser Cys Lys Ala Ser Gly Tyr Pro Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Ser Thr Gly Glu Ser Thr Phe Ala
65                  70                  75                  80

Asp Asp Phe Lys Gly Arg Phe Asp Phe Ser Leu Glu Thr Ser Ala Asn
                85                  90                  95

Thr Ala Tyr Leu Gln Ile Asn Asn Leu Lys Ser Glu Asp Ser Ala Thr
            100                 105                 110

Tyr Phe Cys Ala Arg Trp Glu Val Tyr His Gly Tyr Val Pro Tyr Trp
        115                 120                 125

Gly Gln Gly Thr Thr Val Thr Val Ser Ser Gly Gly Gly Gly Ser Gly
    130                 135                 140

Gly Gly Gly Ser Gly Gly Gly Ser Asp Ile Gln Leu Thr Gln Ser
145                 150                 155                 160

His Lys Phe Leu Ser Thr Ser Val Gly Asp Arg Val Ser Ile Thr Cys
                165                 170                 175

Lys Ala Ser Gln Asp Val Tyr Asn Ala Val Ala Trp Tyr Gln Gln Lys
            180                 185                 190

Pro Gly Gln Ser Pro Lys Leu Leu Ile Tyr Ser Ala Ser Ser Arg Tyr
        195                 200                 205

Thr Gly Val Pro Ser Arg Phe Thr Gly Ser Gly Ser Gly Pro Asp Phe
    210                 215                 220

Thr Phe Thr Ile Ser Ser Val Gln Ala Glu Asp Leu Ala Val Tyr Phe
225                 230                 235                 240
```

Cys Gln Gln His Phe Arg Thr Pro Phe Thr Phe Gly Ser Gly Thr Lys
                245                 250                 255

Leu Glu Ile Lys Ala Leu Ser Asn Ser Ile Met Tyr Phe Ser His Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Ser Arg Pro Ala Ala Gly Gly Ala Val His Thr Arg Gly
305                 310                 315                 320

Leu Asp Lys Pro Phe Trp Val Leu Val Val Val Gly Gly Val Leu Ala
                325                 330                 335

Cys Tyr Ser Leu Leu Val Thr Val Ala Phe Ile Ile Phe Trp Val Arg
            340                 345                 350

Ser Lys Arg Ser Arg Leu Leu His Ser Asp Tyr Met Asn Met Thr Pro
        355                 360                 365

Arg Arg Pro Gly Pro Thr Arg Lys His Tyr Gln Pro Tyr Ala Pro Pro
    370                 375                 380

Arg Asp Phe Ala Ala Tyr Arg Ser Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 16
<211> LENGTH: 1515
<212> TYPE: DNA
<213> ORGANISM: Artificial Sequence
<220> FEATURE:
<223> OTHER INFORMATION: Nucleotide sequence encoding ErbB2-specific
      chimeric antigen receptor

<400> SEQUENCE: 16
atggactgga tctggcggat tctgttcctg gtcggggctg ccacaggcgc ccacagccag      60
gtgcagctgc agcagagcgg ccctgagctg aagaagcccg cgagacagt caagatcagc     120 tgcaaggcca gcggctaccc cttcaccaac tacggcatga actgggtgaa acaggcccca     180
ggccagggac tgaagtggat gggctggatc aacaccagca ccggcgagag caccttcgcc     240
gacgacttca aggcagatt cgacttcagc ctggaaacca cgccaacac cgcctacctg     300 cagatcaaca acctgaagag cgaggacagc gccacctact tttgcgccag atgggaggtg     360
taccacggct acgtgcccta ctggggccag ggcaccaccg tgaccgtgtc cagcggcgga     420
gggggctctg gcggcggagg atctggggga ggggcagcg acatccagct gacccagagc     480

```
                                        -continued cacaagtttc tgagcaccag cgtgggcgac cgggtgtcca tcacctgcaa agccagccag    540
gacgtgtaca acgccgtggc ctggtatcag cagaagcctg gccagagccc caagctgctg    600
atctacagcg ccagcagccg gtacaccggc gtgcccagca ggttcaccgg cagcggcagc    660
ggcccagact tcaccttcac catcagcagc gtgcaggccg aggacctggc cgtgtacttc    720
tgccagcagc acttccggac ccccttcacc ttcggctccg gcaccaagct ggaaatcaag    780
gccctgagca acagcatcat gtacttcagc cacttcgtgc ccgtgtttct gcccgccaag    840
cccaccacca cccctgcccc cagaccccct acccccagccc ccacaatcgc cagccagccc    900
ctgagcctga ggcccgaggc cagcagacct gccgctgggg gagccgtgca caccaggggc    960
ctggacaagc ccttctgggt gctggtcgtg gtcggcggag tgctggcctg ttacagcctg   1020
ctggtcaccg tggccttcat catcttttgg gtccgcagca agcggagccg gctgctgcac   1080
agcgactaca tgaacatgac cccaaggcgg ccaggcccca cccggaagca ctaccagccc   1140
tatgcccctc ctagggactt cgccgcctac cggtccagag tgaagttcag ccgcagcgcc   1200
gacgcccctg cctaccagca gggccagaac cagctgtaca acgagctgaa cctgggcagg   1260
cgggaggaat acgacgtgct ggacaagcgc agaggccggg accctgagat gggcggcaag   1320
cccaggcgga agaaccccca ggaaggcctg tataacgaac tgcagaaaga caagatggcc   1380
gaggcctaca gcgagatcgg catgaagggc gagcggcgac gcggcaaggg ccacgacggc   1440
ctgtaccagg gcctgtccac cgccaccaag gacacctacg acgccctgca catgcaggcc   1500
ctgcctcccc gttaa                                                    1515
```